(12) United States Patent
Donde

(10) Patent No.: US 6,875,787 B2
(45) Date of Patent: Apr. 5, 2005

(54) 10,10-DIALKYL PROSTANOIC ACID DERIVATIVES AS AGENTS FOR LOWERING INTRAOCULAR PRESSURE

(75) Inventor: Yariv Donde, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 261 days.

(21) Appl. No.: 10/365,369

(22) Filed: Feb. 11, 2003

(65) Prior Publication Data

US 2004/0157901 A1 Aug. 12, 2004

(51) Int. Cl.[7] .................. A61K 31/41; C07D 257/02
(52) U.S. Cl. .................. 514/385; 514/443; 514/530; 514/573; 548/253; 549/53
(58) Field of Search .................. 560/121; 562/503; 514/530, 573, 443; 548/253; 549/53

(56) References Cited

U.S. PATENT DOCUMENTS

| | | |
|---|---|---|
| 4,117,014 A | 9/1978 | Pernet et al. |
| 4,994,274 A | 2/1991 | Chan et al. |
| 5,034,413 A | 7/1991 | Chan et al. |
| 5,446,041 A | 8/1995 | Chan et al. |
| 6,531,504 B2 | 3/2003 | Burk et al. |

FOREIGN PATENT DOCUMENTS

JP         59-101458    *  6/1984

OTHER PUBLICATIONS

Bito, L.Z., *Prostaglandins old concepts and new perspectives*, Arch Ophthalmol—vol. 105, Aug. 1987, pp. 1036–10–39.

Bito, L.Z., *Prostaglandins and related compounds as potential ocular therapeutic agents*, Chpt. 18, Biological Protection with Prostaglandins, vol. 1, CRC Press, Inc., M.M. Cohen, Editor.

Bito, L.Z., *Prostaglandins, other eicosanoids, and their derivatives as potential antiglaucoma agents*, Chap. 20, pp. 477–505, Glaucoma: Applied pharmacology in medical treatment, Grune & Stratton, Inc., S.Drance, et al., Editors.

Brooks, D.W., et al., *Asymmetric Microbial Reduction of prochiral 2,2–disubstituted cycloalkanediones*, J. Org. Chem. 1987, 52, 3223–3232.

Nilsson, S., et al. *PGF₂, Increases uveoscieral outflow*, Invest Ophthalmol Vis Sci 1987; 28(3 Suppl) :284.

* cited by examiner

*Primary Examiner*—Joseph K. McKane
*Assistant Examiner*—Kamal Saeed
(74) *Attorney, Agent, or Firm*—Brent A. Johnson; Martin A. Voet; Robert J. Baran

(57) ABSTRACT

The present invention provides a method of treating ocular hypertension or glaucoma which comprises administering to an animal having ocular hypertension or glaucoma therapeutically effective amount of a compound represented by the general formula I;

Formula I

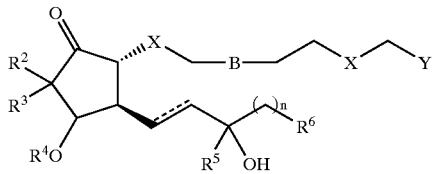

wherein the dashed line indicates the presence or absence of a bond, the hatched wedge indicates the α (down) configuration, and the solid triangle indicates the β (up) configuration;

B is a single, double, or triple covalent bond;

n is 0–6;

X is $CH_2$, S or O;

Y is any pharmaceutically acceptable salt of $CO_2H$, or $CO_2R$, $CONR_2$, $NHCH_2CH_2OH$, $N(CH_2CH_2OH)_2$, $CH_2OR$, $P(O)(OR)_2$, $CONRSO_2R$, $SONR_2$, or

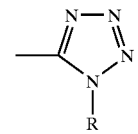

R is H, $C_{1-6}$ alkyl or $C_{2-6}$ alkenyl;

$R^2$ and $R^3$ are $C_{1-6}$ linear alkyl which may be the same or different, and may be bonded to each other such that they form a ring incorporating the carbon to which they are commonly attached;

$R^4$ is hydrogen, R, C(=O)R, or any group that is easily removed under physiological conditions such that $R^4$ is effectively hydrogen;

$R^5$ is hydrogen or R;

$R^6$ is
  iv) hydrogen;
  v) a linear or branched hydrocarbon containing between 1 and 8 carbon atoms, which may contain one or more double or triple bonds, or oxygen or halogen derivatives of said hydrocarbon, wherein 1–3 carbon or hydrogen atoms may be substituted by O or a halogen; or
  vi) aryloxy, heteroaryloxy, $C_{3-8}$ cycloalkyloxy, $C_{3-8}$ cycloalkyl, $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{6-10}$ aryl, $C_{3-10}$ heteroaryl, aryloxy, heteroaryloxy, $C_{1-6}$ alkyl, OR, SR, and $SO_2R$.

Some of the compounds of the present invention and some of their methods of preparation are also novel an nonobvious.

27 Claims, 7 Drawing Sheets

Scheme 1
Equation 1 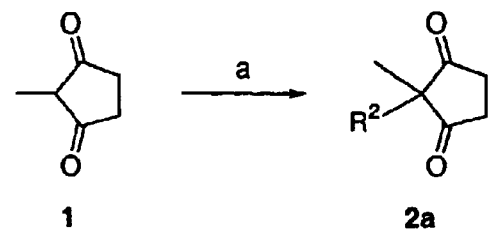
Equation 2 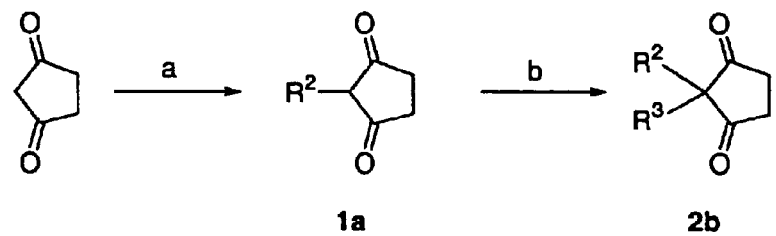
Equation 3 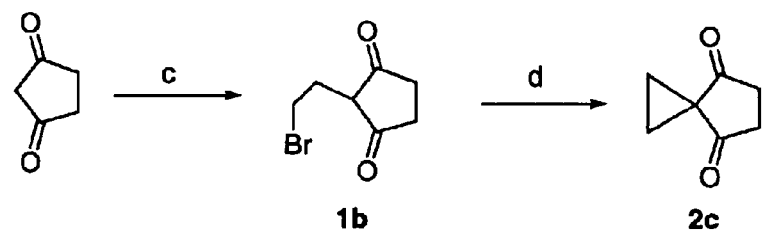
(a) KOH, I-R$^2$, dioxane/H$_2$O; (b) KOH, I-R$^3$, dioxane/H$_2$O; (c) KOH, 1,2-dibromoethane, dioxane/H$_2$O; (d) KOH, dioxane/H$_2$O.

Scheme 2
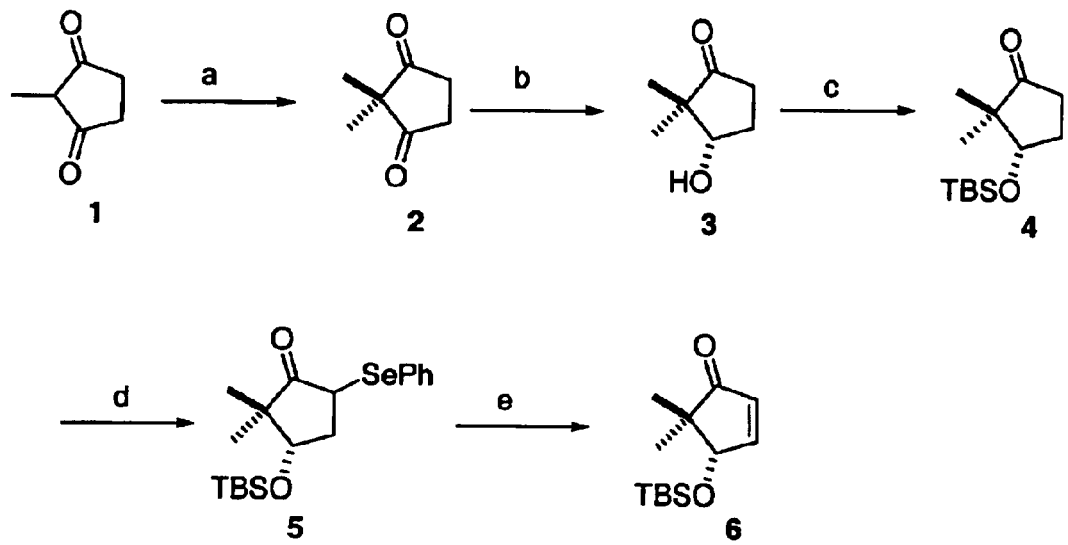
(a) KOH, MeI, dioxane/H$_2$O; (b) Baker's Yeast, D-glucose, H$_2$O; (c) TBSOTf, 2,6-lutidine, CH$_2$Cl$_2$; (d) LDA, THF; PhSeCl; (e) 30% H$_2$O$_2$, CH$_2$Cl$_2$.

Scheme 3
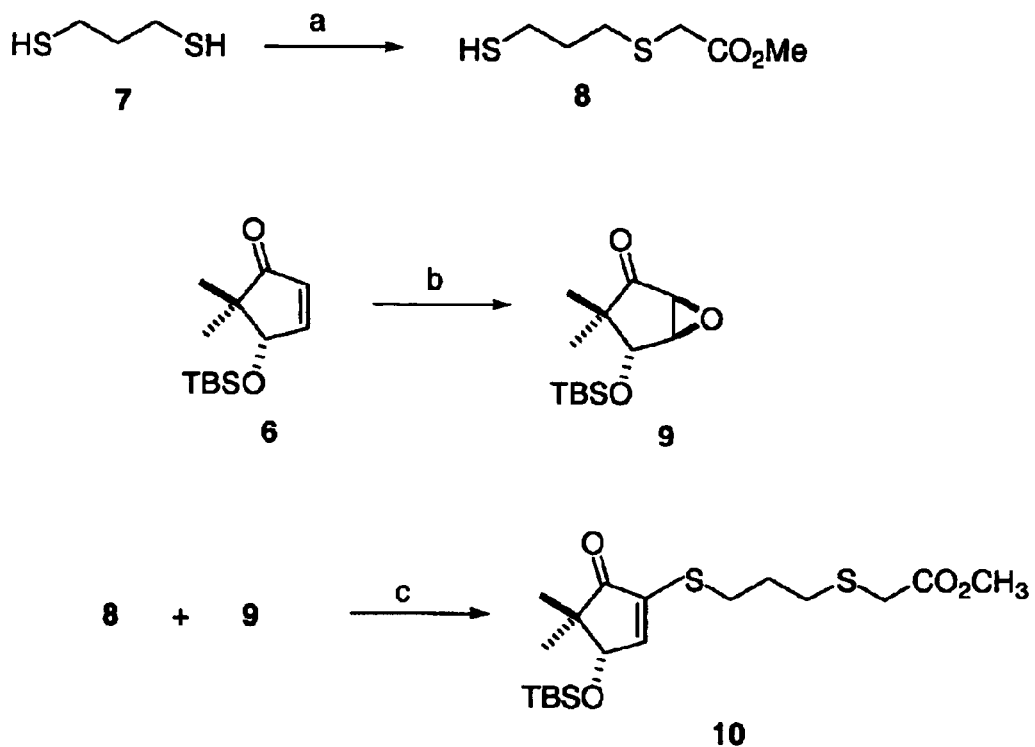
(a) NaH, BrCH$_2$CO$_2$CH$_3$; (b) H$_2$O$_2$, NaOH, MeOH; (c) basic Alumina, CH$_2$Cl$_2$.

Scheme 4
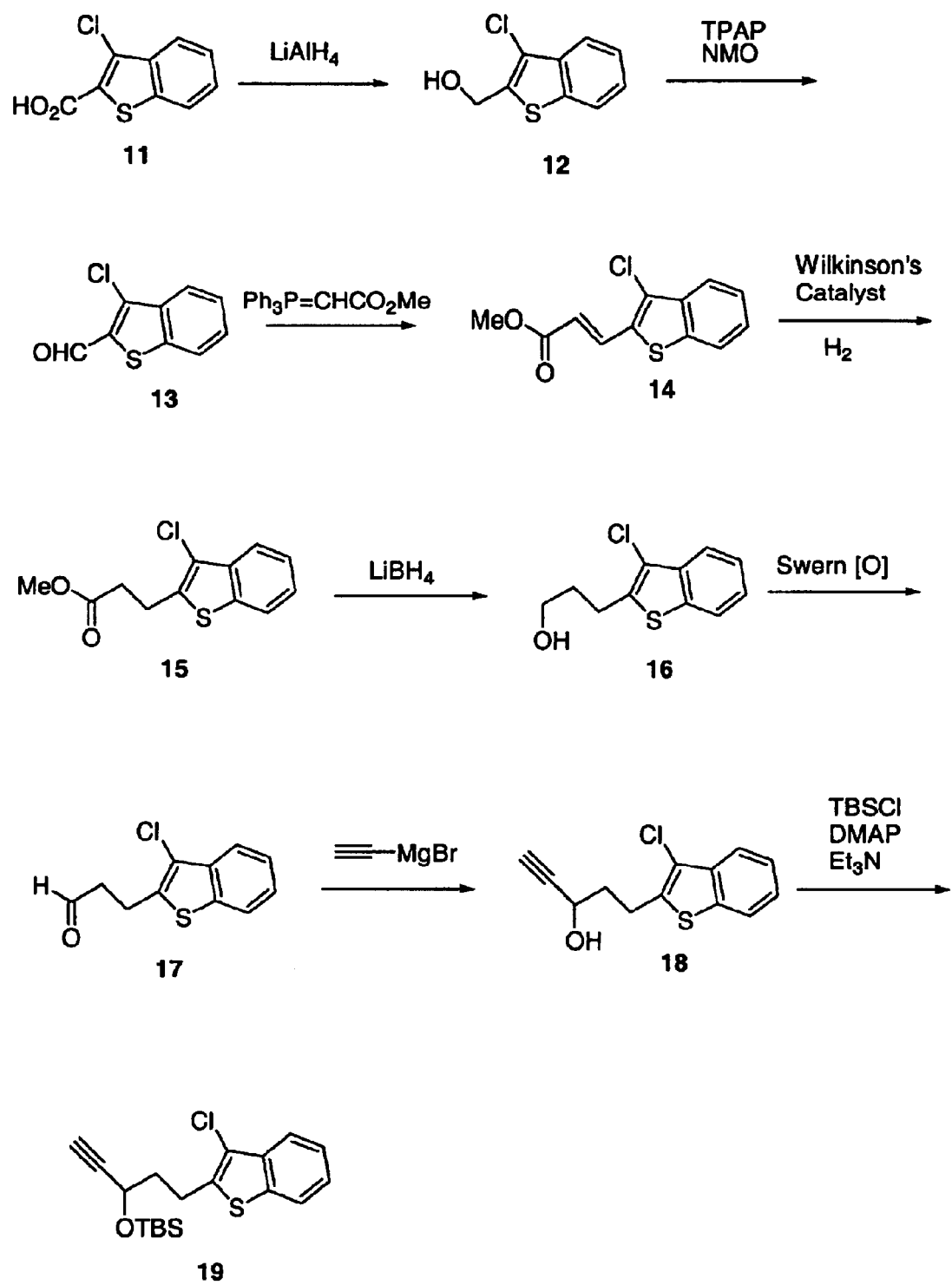

Scheme 5
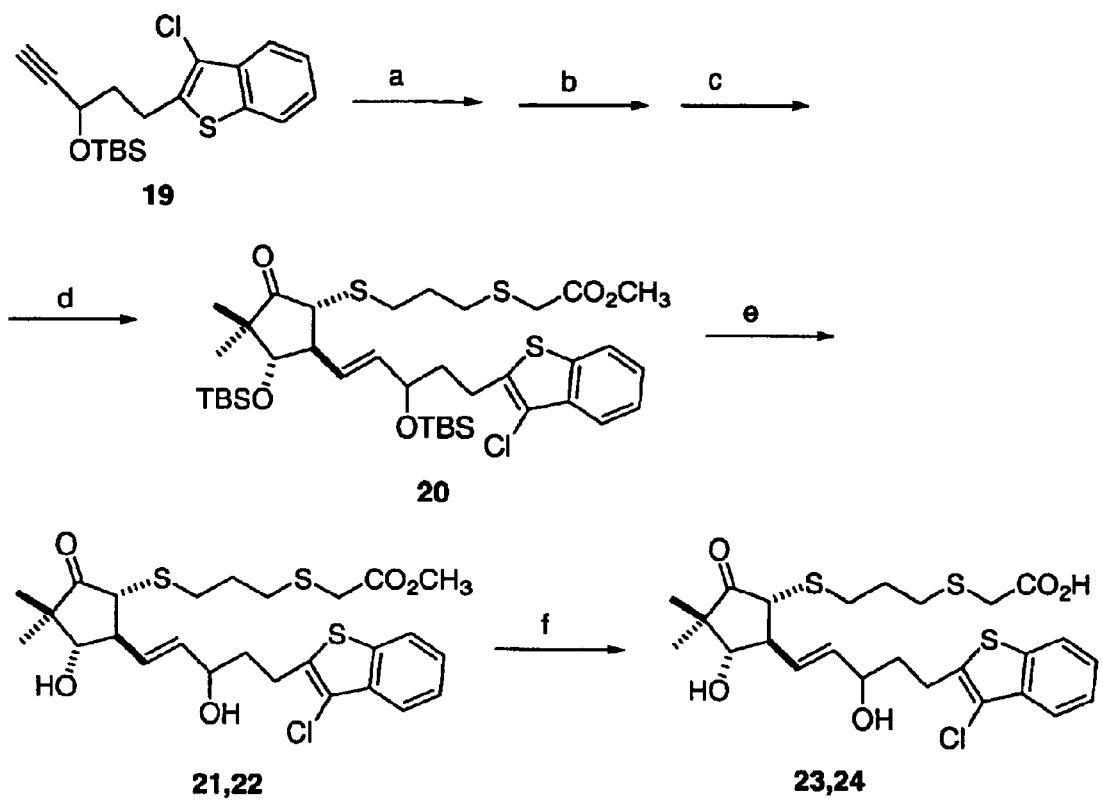
(a) Cp$_2$ZrHCl, THF; (b) MeLi, Et$_2$O -78 °C; (c) lithium 2-thienycyanocuprate;
(d) enone 10, THF -78 °C; (e) HF-pyridine, CH$_3$CN; separate diastereomers
(f) rabbit liver esterase, phosphate buffer, CH$_3$CN.

Scheme 6
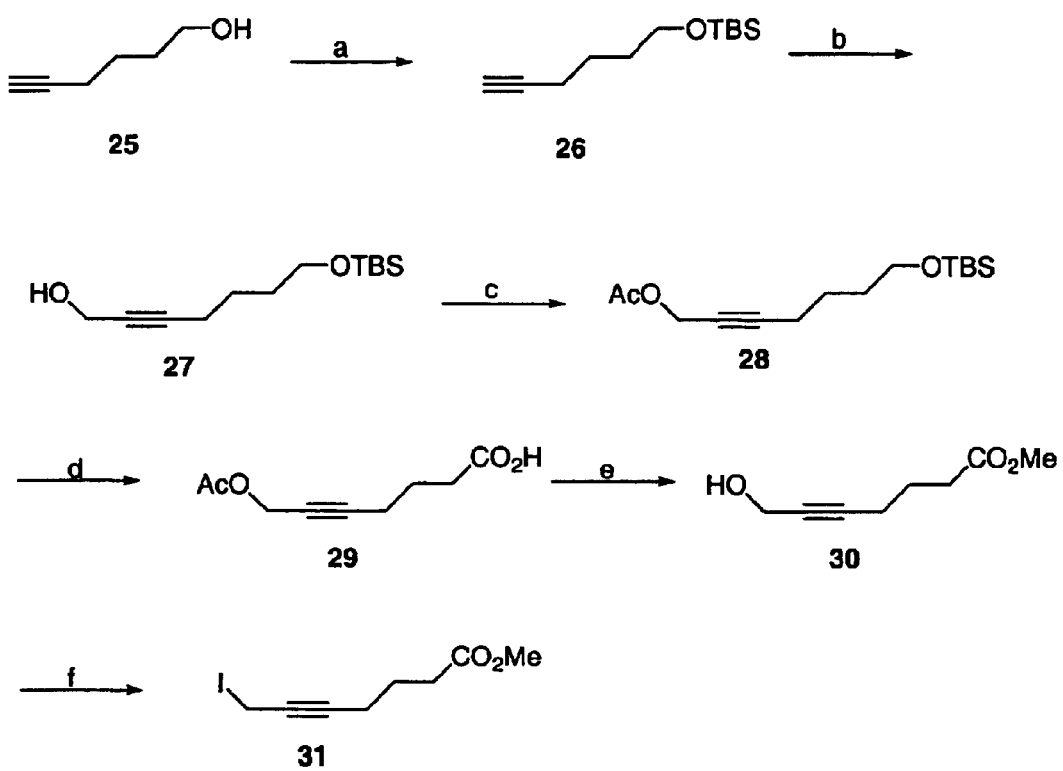
(a) TBSCl, etc.; (b) n-BuLi; DMF; (c) Ac$_2$O, pyridine; (d) Jones oxidation; (e) MeOH, AcCl; (f) PPh$_3$, I$_2$, imidazole, CH$_2$Cl$_2$.

Scheme 7
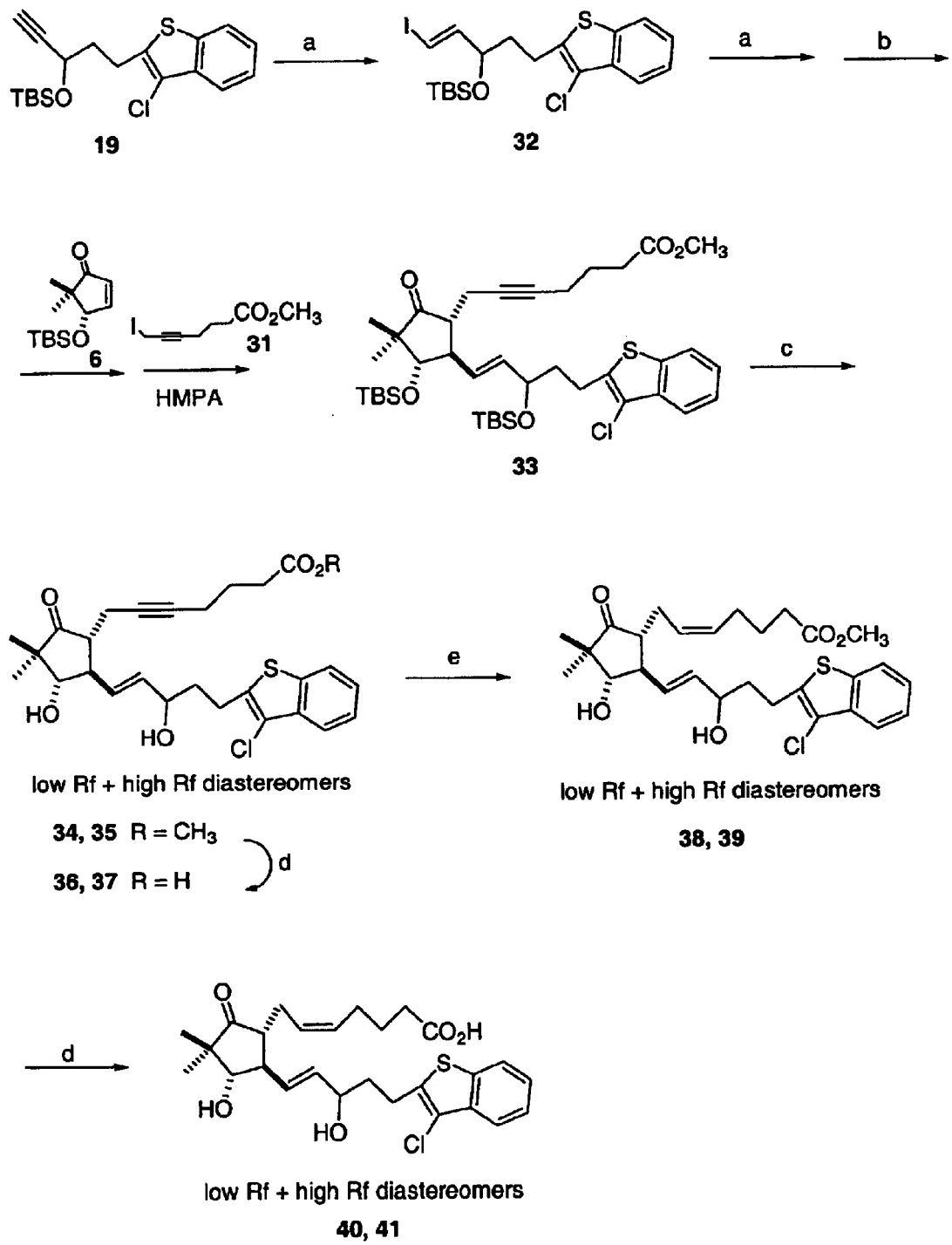
(a) t-BuLi, THF -78 °C; (b) Me₂Zn; (c) HF-pyridine, CH₃CN; separate diastereomers; (d) rabbit liver esterase, pH 7.2 phosphate buffer, CH₃CN; (e) NiCl₂, NaBH₄, ethylenediamine, H₂, THF;

10,10-DIALKYL PROSTANOIC ACID DERIVATIVES AS AGENTS FOR LOWERING INTRAOCULAR PRESSURE

BACKGROUND OF THE INVENTION

1. Field of the Invention

The present invention relates to prostanoic acid derivatives as potent ocular hypotensives that are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

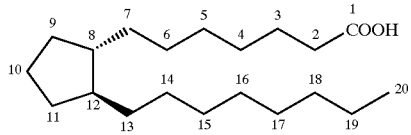

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed 10 Oct. 1990, now U.S. Pat. No. 5,446,041), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175, 476 (filed 29 Dec. 1993). Similarly, 11,15- 9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed 07 Jul. 1989, now U.S. Pat. No. 4,994,274), U.S. Ser.

No. 584,370 (filed 18 Sep. 1990, now U.S. Pat. No. 5,028,624) and U.S. Ser. No. 585,284 (filed 18 Sep. 1990, now U.S. Pat. No. 5,034,413). Recently, we have also shown that 17-napthyl and benzothienyl prostaglandin compounds also have ocular hypotensive activity (U.S. Ser. No. 859,770, filed 17 May 2001). The disclosures of all of these patent applications are hereby expressly incorporated by reference.

Certain 15,15-dimethyl prostaglandins with antihypertensive, gastric acid secretion inhibition, and smooth muscle stimulant properties, are known to have improved metabolic stability. These are described by Pernet et al in U.S. Pat. No. 4,117,014 (filed 23 Dec. 1976), the disclosure of which is hereby expressly incorporated by reference.

SUMMARY OF THE INVENTION

The present invention concerns a method of treating ocular hypertension which comprises administering to a mammal having ocular hypertension a therapeutically effective amount of a compound of Formula I Formula I

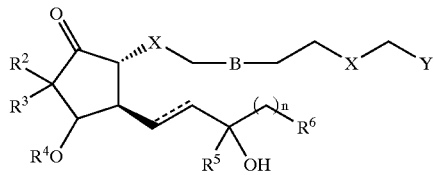

wherein the dashed line indicates the presence or absence of a bond, the hatched wedge indicates the α (down) configuration, and the solid triangle indicates the β (up) configuration;

B is a single, double, or triple covalent bond;

n is 0–6;

X is $CH_2$, S or O;

Y is any pharmaceutically acceptable salt of $CO_2H$, or $CO_2R$, $CONR_2$, $NHCH_2CH_2OH$, $N(CH_2CH_2OH)_2$, $CH_2OR$, $P(O)(OR)_2$, $CONRSO_2R$, $SONR_2$, or

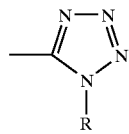

R is H, $C_{1-6}$ alkyl or $C_{2-6}$ alkenyl;

$R^2$ and $R^3$ are $C_{1-6}$ linear alkyl which may be the same or different, and may be bonded to each other such that they form a ring incorporating the carbon to which they are commonly attached;

$R^4$ is hydrogen, R, C(=O)R, or any group that is easily removed under physiological conditions such that $R^4$ is effectively hydrogen;

$R^5$ is hydrogen or R;

$R^6$ is
 i) hydrogen;
 ii) a linear or branched hydrocarbon containing between 1 and 8 carbon atoms, which may contain one or more double or triple bonds, or oxygen or halogen derivatives of said hydrocarbon, wherein 1–3 carbon or hydrogen atoms may be substituted by O or a halogen; or iii) aryloxy, heteroaryloxy, $C_{3-8}$ cycloalkyloxy, $C_{3-8}$ cycloalkyl, $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{6-10}$ aryl, $C_{3-10}$ heteroaryl, aryloxy, heteroaryloxy, $C_{1-6}$ alkyl, OR, SR, and $SO_2R$.

In another aspect, the present invention relates to a pharmaceutical product, comprising a container adapted to dispense its contents in a metered form; and an ophthalmic solution therein, as hereinabove defined.

In another aspect, certain of the compounds represented by the above formula, disclosed below and utilized in the method of the present invention are novel and unobvious.

In a further aspect, certain elements of the processes of preparing the compounds represented by the above formula and described herein are novel and unobvious.

BRIEF DESCRIPTION OF THE DRAWING FIGURES

Schemes 1–7 illustrate possible ways to prepare compounds of the invention.

DETAILED DESCRIPTION OF THE INVENTION

The present invention relates to the use of prostanoic acid derivatives as ocular hypotensives. The compounds used in accordance with the present invention are encompassed by the following structural formula I:

Formula I

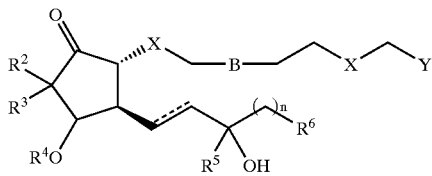

A preferred group of the compounds of the present invention includes compounds that do not have the following structural formula II:

Formula II

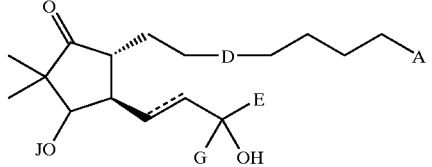

wherein

A is $CO_2H$ or $CO_2Me$;

D is a single, double, or triple covalent bond;

E is a linear, branched, or cycloalkyl chain of 3 to 7 carbons, trifluoromethylbutyl, hydroxylalkyl, or $CH_2R^7$ wherein $R^7$ is phenyl, cyclopentyl, phenoxy, chlorophenoxy, propoxy, or $—CH_2SCH_2CH_3$;

J is hydrogen, R, C(=O)R, or any group that is easily removed under physiological conditions such that $R^4$ is effectively hydrogen; and G is H or $CH_3$.

Another preferred group includes compounds having formula III:

Formula III

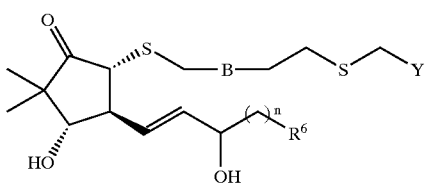

Another preferred group includes compounds having formula IV:

Formula IV

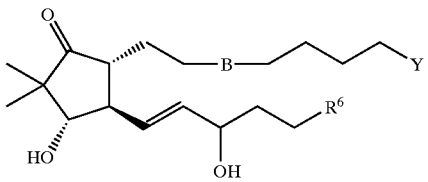

Another preferred group includes compounds having formula V:

Formula V

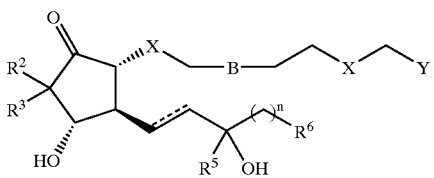

wherein at least one of $R^2$ and $R^3$ is not methyl.

In the above formulae, the substituents and symbols are as hereinabove defined.

In the above formulae:
Preferably Y is any pharmaceutically acceptable salt of $CO_2H$ or $CO_2R$. More preferably Y is $CO_2H$ or $CO_2Me$.
Preferably n is 2.
Preferably, $R^6$ is $C_{6-10}$ aryl or $C_{3-10}$ heteroaryl, which may contain one or more substituents selected from the group consisting of halogen, trihalomethyl, cyano, nitro, amino, hydroxy, $C_{1-6}$ alkyl, OR, SR, and $SO_2R$. More preferably $R^6$ is phenyl, napthyl, benzofuranyl, or benzothienyl, which may contain one or more substituents selected from the group consisting of halogen, trihalomethyl, cyano, nitro, amino, hydroxy, $C_{1-6}$ alkyl, OR, SR, and $SO_2R$. Most preferred is 3-chlorobenzothien-2-yl.

Another preferred group includes compounds having formula XIII:

Formula XIII

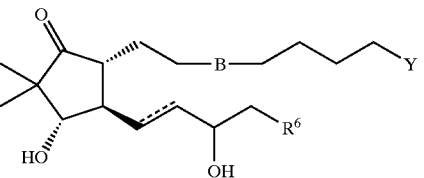

wherein B represents a single or double bond;
and $R^6$ is napthyl, benzofuranyl, or benzothienyl, which may contain one or more substituents selected from the group consisting of halogen, trihalomethyl, cyano, nitro, amino, hydroxy, $C_{1-6}$ alkyl, OR, SR, and $SO_2R$.

In another aspect of this invention, certain elements of the method making the compounds of the invention are novel and unobvious. One such novel and unobvious element is the application of the use of Baker's yeast as a reducing agent as reported by Brooks and coworkers (Brooks, et. al., "Asymmetric Microbial Reduction of Prochiral 2,2-Disubstituted Cycloalkanediones", *J. Org. Chem.*, 1987, 52, 3223–3232) in the synthesis of compounds of this invention. In this novel and unobvious application of this reaction, Baker's yeast is used to carry out an asymmetric reduction of a compound of formula VII, which is a 2,2-dialkylcyclopentane-1,3-dione, to a compound of formula VIII, which is a 2,2-dialkyl-3(S)-hydroxycyclopentanone. A compound of formula VIII is then used to prepare compounds of this invention.

Formula VI

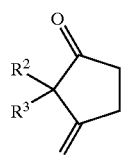

Formula VII

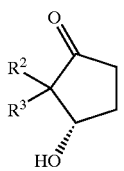

The two alkyl groups, $R^2$ and $R^3$ of the compounds of formula VI and VII, in this reaction are the same as those defined for compounds of Formula I above. In the case where the two alkyl groups are different, a mixture of diastereomers is formed, which can be separated by conventional separation methods to obtain the enantiomerically pure products.

Preparation of 2,2-dialkylcyclopentan-1,3-diones is well known in the art. One convenient way that a large variety of these compounds can be prepared is by base-mediated alkylation of carbon-2 of the cyclopentane-1,3-dione using an alkyl halide or equivalent compound. This type of reaction is well known in the art. The preparation of three general types of 2,2-dialkylcyclopentan-1,3-diones using this alkylation reaction is illustrated in Scheme 1. Compounds where one of the alkyl groups is methyl can be prepared by a simple alkylation reaction from commercially available 2-methylcyclopentan-1,3-dione 1 (Equation 1). In the case neither of the alkyl groups in the 2,2-dialkylcyclopentan-1,3-dione are methyl (compound 2b), these compounds can be prepared from cyclopentan-1,3-dione by two consecutive alkylation reactions (Equation 2). In the case where the two alkyl groups in the 2,2-dialkylcyclopentan-1,3-dione are the same, these alkylation reactions can be carried out in a one-pot procedure. In the case where the two alkyl groups to form a cyclic compound incorporating $C_2$ of the cyclopentanone into the ring, otherwise known as a spiroketone, these compounds can be prepared by using a dihaloalkane or equivalent compound to carry out a intermolecular alkylation followed by an intramolecular alkylation (Equation 3), which could be carried out in a one or two pot process. Those skilled in the art will recognize that there are many ways to prepare 2,2-dialkylcyclopentan-1,3-diones, and the reactions of Scheme 1 are included to illustrate that these compounds can be readily prepared or obtained by those skilled in the art, and are not intended to limit the scope of the invention in any way.

In another novel and unobvious aspect of this invention, compounds of the invention represented by Formula VIII are prepared by a process that comprises the following steps:

Formula VIII

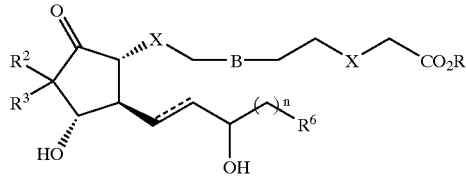

i) reacting a compound of Formula IX with a compound of Formula X in the presence of a suitable base to form a compound of Formula XI;

Formula IX

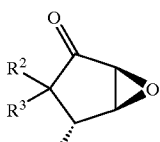

Formula X

HX—B—X—CO₂R (rendered: $HX{-}B{-}X{-}CO_2R$)

Formula XI

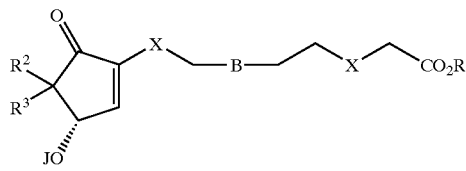

ii) coupling a compound of Formula XI with a compound of Formula XII; and

Formula XII

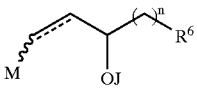

iii) removing the protecting groups and separating the diastereomers to obtain the desired products;

wherein the hatched wedges indicate the α (down) configuration, the solid triangles indicate the β (up) configuration, and the wavy lines indicate either the cis (Z) or trans (Z) conformation;

n is 0–6;

B is a single, double, or triple covalent bond;

J is a protecting group that can be easily removed to form the respective hydroxide group without affecting the rest of the molecule;

R is $C_{1-6}$ alkyl or $C_{2-6}$ alkenyl;

$R^2$ and $R^3$ are $C_{1-6}$ linear alkyl which may be the same or different, and may be bonded to each other such that they form a ring incorporating the carbon to which they are commonly attached;

X is S or O; and

M is a group that comprises one or more metal atoms.

All of the compounds encompassed by this invention can be prepared using the methods described above supplemented by methods known to those skilled in the art. The synthesis of several compounds of the invention is illustrated in Schemes 2–7. These Schemes that are included herein are merely illustrative and are not intended to limit the scope of the invention in any way. Although there are several ways the reduction of compounds of Formula VI to Formula VII could be incorporated into the synthesis of these compounds, one convenient way to this is shown in Scheme 2. In this Scheme, compound 2 is a compound of Formula VI and compound 3 is a compound of formula VII. However, those skilled in the art will recognize that there are many ways in which the reduction could be used to prepare compounds of this invention.

TABLE 1

| Structure | Low Rf diastereomer | High Rf diastereomer |
|---|---|---|
| 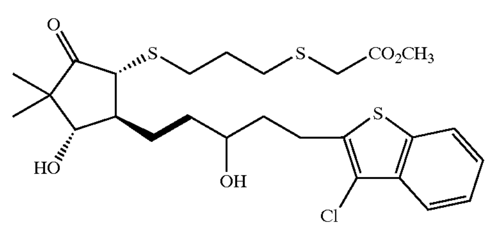 | 21 | 22 |
| 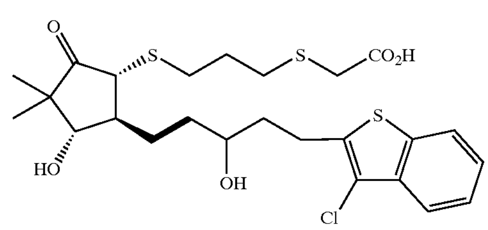 | 23 | 24 |

TABLE 1-continued

| Structure | Low Rf diastereomer | High Rf diastereomer |
|---|---|---|
| 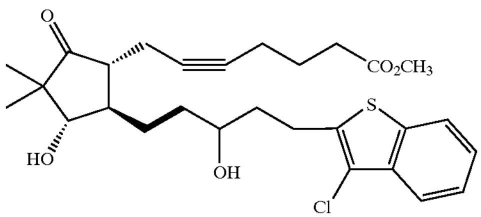 | 34 | 35 |
| 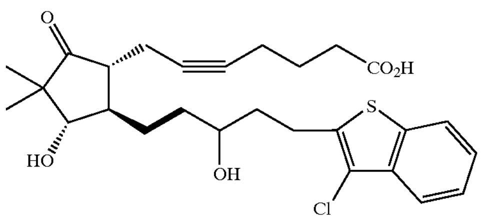 | 36 | 37 |
| 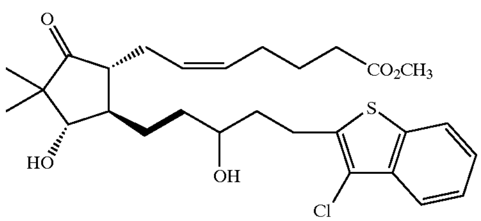 | 38 | 39 |
| 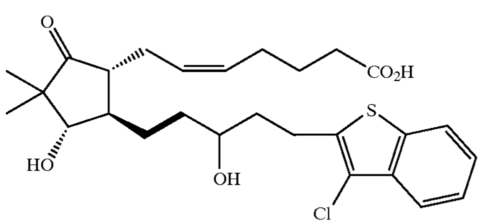 | 40 | 41 |
| 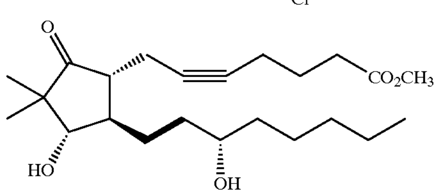 | 42 | |
| 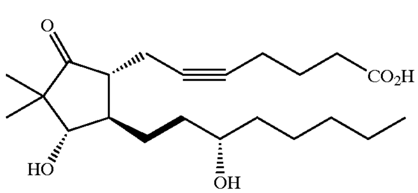 | 43 | |
| 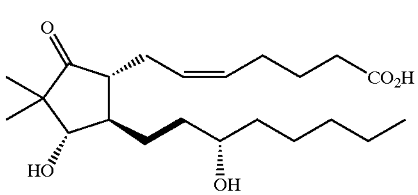 | 44 | |

TABLE 1-continued

| Structure | Low Rf diastereomer | High Rf diastereomer |
|---|---|---|
| (structure with CO₂CH₃, OH, HO) | | 45 |
| (structure with CO₂H, OH, HO, phenyl) | 46 | 47 |
| (structure with CO₂CH₃, OH, HO, phenyl) | 48 | 49 |
| (structure with CO₂CH₃, OH, HO, phenyl) | 50 | 51 |
| (structure with CO₂H, OH, HO, phenyl) | 52 | 53 |
| (structure with CO₂H, OH, HO, benzothiophene) | 54 | 55 |
| (structure with CO₂H, OH, HO, benzothiophene) | 56 | 57 |

TABLE 1-continued

| Structure | Low Rf diastereomer | High Rf diastereomer |
|---|---|---|
| (structure) | 58 | 59 |
| (structure) | 60 | 61 |
| (structure) | 62 | 63 |
| (structure) | 64 | 65 |
| (structure) | 66 | 67 |

The compounds named below, and illustrated in Table 1, are especially preferred representatives of the compounds of the present invention:

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid methyl ester (21, 22);

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid (23, 24);

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid methyl ester (34, 35);

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid (36, 37);

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (38,39);

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid (40, 41);

7-[(1R,4S,5R)-4-Hydroxy-5-((E)-(S)-3-hydroxy-oct-1-enyl)-3,3-dimethyl-2-oxo-cyclopentyl]-hept-5-ynoic acid methyl ester (42)

7-[(1R,4S,5R)-4-Hydroxy-5-((E)-(S)-3-hydroxy-oct-1-enyl)-3,3-dimethyl-2-oxo-cyclopentyl]-hept-5-ynoic acid (43)

(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid (44)

(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid methyl ester (45)

(Z)-7-[(1R,4S,5R)-4-Hydroxy-5-((E)-3-hydroxy-4-phenyl-but-1-enyl)-3,3-dimethyl-2-oxo-cyclopentyl]-hept-5-enoic acid (46, 47)

(Z)-7-[(1R,4S,5R)-4-Hydroxy-5-((E)-3-hydroxy-4-phenyl-but-1-enyl)-3,3-dimethyl-2-oxo-cyclopentyl]-hept-5-enoic acid methyl ester (48, 49)

(Z)-7-[(1R,4S,5R)-4-Hydroxy-5-((E)-3-hydroxy-5-phenyl-pent-1-enyl)-3,3-dimethyl-2-oxo-cyclopentyl]-hept-5-enoic acid methyl ester (50,51)

(Z)-7-[(1R,4S,5R)-4-Hydroxy-5-((E)-3-hydroxy-5-phenyl-pent-1-enyl)-3,3-dimethyl-2-oxo-cyclopentyl]-hept-5-enoic acid (52,53)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (54,55)

7-[(1R,4S,5R)-5-((E)-4-Benzo[b]thiophen-2-yl-3-hydroxy-but-1-enyl)-4-hydroxy-3,3-dimethyl-2-oxo-cyclopentyl]-heptanoic acid (56,57)

(Z)-7-[(1R,4S,5R)-5-(4-Benzo[b]thiophen-2-yl-3-hydroxy-butyl)-4-hydroxy-3,3-dimethyl-2-oxo-cyclopentyl]-hept-5-enoic acid (58,59)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid ethylamide (60,61)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid diethylamide (62,63)

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl)-hept-5-enoic acid (2-hydroxy-ethyl)-amide (64,65)

(3S,4R,5R)-4-((E)-4-Benzo[b]thiophen-2-yl-3-hydroxy-but-1-enyl)-3-hydroxy-2,2-dimethyl-5-[(Z)-6-(1-H-tetrazol-5-yl)-hex-2-enyl]-cyclopentanone (66,67)

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

SYNTHETIC EXAMPLES

The methods of preparing compounds of this invention are further illustrated by the following non-limiting Examples, which are summarized in the reaction schemes of FIGS. 1–7 wherein the compounds are identified by the same designator in both the Examples and the Figures.

2-Alkyl-cyclopentane-1,3-dione (1a). A mixture of 1,3-cyclopentanedione (89.4 mmol, Aldrich), I-R$^2$ (96.4 mmol, Aldrich), and KOH (5.097 g, 90.8 mmol) in H$_2$O (25 mL)/dioxane (75 mL) is heated at reflux. After 5 h, a solution of KOH (2 g) and I-R$^2$ (2 mmol) in H$_2$O (5 mL)/dioxane (15 mL) is added and after another 3 h at reflux the solution is allowed to stir at room temperature overnight. In the morning, the reaction is continued by addition of a solution of KOH (2 g) and I-R$^2$ (2.4 mmol) in H$_2$O (5 mL)/dioxane (15 mL) and heating at reflux. After 4 h, the mixture is allowed to cool to room temperature and is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of NaHCO$_3$ solution (150 mL, saturated) and the resulting mixture is then extracted with CH$_2$Cl$_2$ (4×75 mL). The combined CH$_2$Cl$_2$ solution is dried (MgSO$_4$), filtered and evaporated to leave a brown oil which is used directly in the next step.

2-Alkyl-2-methyl-cyclopentane-1,3-dione (2a). A mixture of 2-methyl-1,3-cyclopentanedione (10.025 g, 89.4 mmol, Aldrich), I-R$^2$ (96.4 mmol, Aldrich), and KOH (5.097 g, 90.8 mmol) in H$_2$O (25 mL)/dioxane (75 mL) is heated at reflux. After 5 h, a solution of KOH (2 g) and I-R$^2$ (2 mmol) in H$_2$O (5 mL)/dioxane (15 mL) is added and after another 3 h at reflux the solution is allowed to stir at room temperature overnight. In the morning, the reaction is continued by addition of a solution of KOH (2 g) and I-R$^2$ (2.4 mmol) in H$_2$O (5 mL)/dioxane (15 mL) and heating at reflux. After 4 h, the mixture is allowed to cool to room temperature and is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of NaHCO$_3$ solution (150 mL, saturated) and the resulting mixture is then extracted with CH$_2$Cl$_2$ (4×75 mL). The combined CH$_2$Cl$_2$ solution is dried (MgSO$_4$), filtered and evaporated to leave a brown oil which is used directly in the next step.

2,2-Dialkyl-methyl-cyclopentane-1,3-dione (2b). A mixture of 2-alkyl-1,3-cyclopentanedione 1a (89.4 mmol, Aldrich), I-R$^3$ (96.4 mmol, Aldrich), and KOH (5.097 g, 90.8 mmol) in H$_2$O (25 mL)/dioxane (75 mL) is heated at reflux. After 5 h, a solution of KOH (2 g) and I-R$^3$ (2 mmol) in H$_2$O (5 mL)/dioxane (15 mL) is added and after another 3 h at reflux the solution is allowed to stir at room temperature overnight. In the morning, the reaction is continued by addition of a solution of KOH (2 g) and I-R$^3$ (2.4 mmol) in H$_2$O (5 mL)/dioxane (15 mL) and heating at reflux. After 4 h, the mixture is allowed to cool to room temperature and is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of NaHCO$_3$ solution (150 mL, saturated) and the resulting mixture is then extracted with CH$_2$Cl$_2$ (4×75 mL). The combined CH$_2$Cl$_2$ solution is dried (MgSO$_4$), filtered and evaporated to leave a brown oil which is used directly in the next step.

Spiro[2.4]heptane-4,7-dione (2c). A mixture of 2-alkyl-1,3-cyclopentanedione 1a (89.4 mmol, Aldrich), 1,2-dibromoethane (120 mmol, Aldrich), and KOH (5.097 g, 90.8 mmol) in H$_2$O (25 mL)/dioxane (75 mL) is heated at reflux for 24 hours. The mixture is allowed to cool, and the crude product is extracted with ether (1×100 mL, 3×75 mL). The combined ether extracts are evaporated, the residue is combined with HCl (50 mL 10%), and the resulting mixture is placed in a 120° C. oil bath until boiling is observed (ca. 15 min.). The mixture is then allowed to cool to room temperature, is neutralized by addition of NaHCO$_3$ solution (150 mL, saturated) and the resulting mixture is then extracted with CH$_2$Cl$_2$ (4×75 mL). The combined CH$_2$Cl$_2$ solution is dried (MgSO$_4$), filtered and evaporated to leave a brown oil which is used directly in the next step.

2,2-Dimethyl-cyclopentane-1,3-dione (2). The published procedure was followed. (Agosta, W. C.; Smith, A. B. J. Org. Chem. 1970, 35, 3856) A mixture of 2-methyl-1,3-cyclopentanedione (10.025 g, 89.4 mmol, Aldrich), methyl iodide (6.0 mL, 96.4 mmol, Aldrich), and KOH (5.097 g, 90.8 mmol) in H$_2$O (25 mL)/dioxane (75 mL) was heated at reflux. After 5 h, a solution of KOH (2 g) and MeI (2.4 mL) in H$_2$O (5 mL)/dioxane (15 mL) was added and after another 3 h at reflux the solution was allowed to stir at room temperature overnight. In the morning, the reaction was continued by addition of a solution of KOH (2 g) and MeI (2.4 mL) in H$_2$O (5 mL)/dioxane (15 mL) and heating at reflux. After 4 h, the mixture was allowed to cool to room temperature and was extracted with ether (1×100 mL, 3×75 mL). The combined ether extracts were evaporated, the residue combined with HCl (50 mL 10%), and the resulting mixture was placed in a 120° C. oil bath until boiling was observed (ca. 15 min.). The mixture was then allowed to cool to room temperature, was neutralized by addition of NaHCO$_3$ solution (150 mL, saturated) and the resulting mixture then extracted with CH$_2$Cl$_2$ (4×75 mL). The combined CH$_2$Cl$_2$ solution was dried (MgSO$_4$), filtered and evaporated to leave a brown oil (10.474 g, 83 mmol, 93%) which was used directly in the next step.

(S)-3-Hydroxy-2,2-dimethyl-cyclopentanone (3). The published procedure was followed. (Brooks, D. W.; Hormoz, M.; Grothaus, P. G. J. Org. Chem. 1987, 52, 3223) A 35° C. (internal temperature) solution of D-glucose (106.73 g, 592 mmol, Aldrich) in H$_2$O (690 mL) in a 4 L Erlenmeyer was treated with baker's yeast (71.065 g, Fleischmann's). The mixture was allowed to ferment for 2 h, then 2,2-dimethyl-cyclopentane-1,3-dione (2) (7.316 g, 58 mmol) was added.

The mixture was stirred for 48 h and then filtered through celite, washing with about 1 L CH$_2$Cl$_2$. The filtration was difficult due to the thick consistency of the yeast and it helped to continually add CH$_2$Cl$_2$ to the mixture and scrape the top of the celite layer with a spatula. The filtrate was transferred to a separatory funnel, and 100 mL brine was added and the layers were separated. Brine (400 mL) was added to the aqueous layer and the resulting solution extracted further with CH$_2$Cl$_2$ (3×500 mL). The combined CH$_2$Cl$_2$ solution was dried (MgSO$_4$), filtered and evaporated to leave a yellow oil. Flash chromatography (11×5 cm, 20% EtOAc/hexs→25%→30%→40%→50%) gave alcohol 3 (2.435 g, 19 mmol, 33%).

The enantiomeric excess of 3 was assayed by $^1$H NMR of the corresponding Mosher's ester which was prepared by treatment of alcohol 3 (11 mg, 0.09 mmol) in dichloroethane (0.3 mL, Aldrich) with pyridine (27 μL, 0.33 mmol; Aldrich) and (R)-α-methoxy-α-trifluoromethyphenylacetic acid chloride (58 μL, 0.31 mmol, Fluka). The mixture was stirred overnight and then partitioned between water (10 mL) and ether (10 mL). The ether layer was washed with 1 M HCl (10 mL) and saturated NaHCO$_3$ solution and then was dried (MgSO$_4$), filtered and evaporated. $^1$H NMR analysis was done on the crude ester.

(S)-3-(tert)-Butyl-dimethyl-silanyloxy-2,2-dimethyl-cyclopentanone (4). A solution of alcohol 3 (520 mg, 4.1 mmol) and 2,6-lutidine (0.56 mL, 4.8 mmol, Aldrich) in CH$_2$Cl$_2$ (8.0 ml, Aldrich) was treated with TBSOTf (1.0 mL, 4.3 mmol, Aldrich). After 5.5 h, saturated NaHCO$_3$ solution (20 mL) was added and the mixture extracted with CH$_2$Cl$_2$ (20 mL). The CH$_2$Cl$_2$ solution was washed with 20 mL each of 1 M HCl, saturated NaHCO$_3$ solution, and brine and then was dried (MgSO$_4$), filtered and evaporated. Flash chromatography (5×5 cm, 10% Et$_2$O/pentane) gave TBS ether 4 (698 mg, 2.9 mmol, 70%).

(S)-3-(tert)-Butyl-dimethyl-silanyloxy-2,2-dimethyl-5-phenylselanyl-cyclopentanone (5). A solution of TBS ether 4 (1.496 g, 6.2 mmol) in THF (2 mL, Aldrich) was added dropwise to a −78° C. solution of LDA (4.9 mL, 7.3 mmol, 1.5 M/cyclohexane, Aldrich) in THF (22 mL, Aldrich), rinsing with 2 mL THF. After 15 min., a solution of PhSeCl (1.424 g, 7.4 mmol, Aldrich) in THF (2 mL) was quickly added by cannula, rinsing with 2 mL THF. The solution was stirred for 10 min. and then partitioned between 50 mL 0.5 M HCl and 75 mL ether. The ether layer was washed with 30 mL each of water, saturated $NaHCO_3$ solution, and brine and then was dried ($MgSO_4$), filtered and evaporated. Flash chromatography (2% EtOAc/hexs→4%) gave phenylselenide 5 (1.641 g, 4.1 mmol, 67%) along with 476 mg of mixed fractions containing a lower $R_f$ impurity.

(S)-4-(tert)-Butyl-dimethyl-silanyloxy-5,5-dimethyl-cyclopent-2-enone(6). A solution of selenide 5 (1.641 g, 4.1 mmol) and pyridine (0.62 mL, 7.7 mmol, Aldrich) in $CH_2Cl_2$ (13 mL, Aldrich) was treated with $H_2O$ (1 mL) and 30% $H_2O_2$ (1.1 mL, Aldrich). The mixture was stirred for 30 min. and then was partitioned between 25 mL $CH_2Cl_2$ and 25 mL saturated $NaHCO_3$ solution. The aqueous layer was extracted with 25 mL $CH_2Cl_2$ and the combined $CH_2Cl_2$ solution washed with 1 M HCl (2×25 mL) and brine (50 mL). The solution was then dried ($MgSO_4$), filtered and evaporated to leave an orange oil. Flash chromatography (6×4 cm, 10% ether/pentane) gave enone 6 (572 mg, 2.4 mmol, 59%).

(3-Mercapto-propylsulfanyl)-acetic acid methyl ester (8). An ice-cold solution of 1,3-dithiane (2.0 mL, 19.9 mmol) in THF (40 mL) was treated with NaH (819 mg, 20.5 mmol). After 30 min., methyl bromoacetate (1.9 mL, 20.0 mmol) was added and the mixture stirred for 3.5 h at room temperature. The reaction was quenched by addition of MeOH and then 50 mL 1 M HCl. The mixture was extracted with ether (2×50 mL) and the combined ether solution washed with saturated sodium bicarbonate solution (50 mL) and brine (50 mL) and then was dried ($MgSO_4$), filtered and evaporated. Purification by flash chromatography on silica gel (10–15% ethyl acetate/hexanes) gave 971 mg (5.38 mmol, 27%) of the thiol.

{3-[(S)-3-(tert)-Butyl-dimethyl-silanyloxy)-4,4-dimethyl-5-oxo-cyclopent-1-enylsulfanyl]-propylsulfanyl}-acetic acid methyl ester (10). A solution of enone 6 (156 mg, 0.65 mmol) in MeOH (4.3 mL) was treated with 30% $H_2O_2$ (0.21 mL) and 1 M NaOH (32 µL). After 4 h, 20 mL saturated ammonium chloride solution was added and the mixture was extracted with dichloromethane (3×10 mL). The combined dichloromethane solution was dried ($Na_2SO_4$), filtered and evaporated in vacuo.

A solution of thiol 8 (110 mg, 0.61 mmol) in dichloromethane (3 mL) was added to the crude epoxide (9) by cannula, rinsing with 1.2 mL. Basic alumina (628 mg) was added and the mixture stirred for 16 h. The solvent was evaporated and purification of the residue by flash chromatography on silica gel (15% ethyl acetate/hexanes) gave 129 mg (0.31 mmol, 48%) of the coupled enone (10).

(3-Chloro-benzo[b]thiophen-2-yl)-methanol (12). To an ice cold solution of 10.0 g (47.0 mmol) of 3-chloro-benzo[b]thiophene-2-carboxylic acid (11) in 200 mL of THF was added 47 mL of $LiAlH_4$ (47 mmol, 1 M/THF). After 3 h, the reaction was quenched by addition of MeOH (ca. 40 mL). The volatiles were evaporated and the residue was treated with 50 mL 1 M HCl. After stirring for 10 min., the mixture was extracted with $CH_2Cl_2$ (3×150 mL). The combined $CH_2Cl_2$ solution was dried ($MgSO_4$), filtered and evaporated. Purification by flash chromatography on silica gel (10–20% ethyl acetate/hexane) gave 4.32 g (21.6 mmol, 46%) of the alcohol (12).

3-Chloro-benzo[b]thiophene-2-carbaldehyde (13). A solution of alcohol 12 (4.32 g, 21.6 mmol) in 40 mL of $CH_2Cl_2$ was treated with 4A molecular sieves, NMO (3.81 g, 32.5 mmol), and TPAP (381 mg, 1.08 mmol). The reaction was stirred for 10 min. and then was evaporated to dryness. Purification by flash chromatography on silica gel (2% ethyl acetate/hexane) gave 3.52 g (18.3 mmol, 84%) of the aldehyde (13).

(E)-3-(3-Chloro-benzo[b]thiophen-2-yl)-acrylic acid methyl ester (14). A solution of 3.52 g (18.3 mmol) of 13 in 50 mL toluene was treated with methyl (triphenylphosphoranylidene)acetate (7.48 g, 21.9 mmol). After 4 h, saturated $NaHCO_3$ solution (50 mL) was added and the mixture extracted with ethyl acetate (2×75 mL). The combined ethyl acetate solution was washed with brine (50 mL), dried ($Na_2SO_4$), filtered and evaporated. Purification by flash chromatography on silica gel (5% ethyl acetate/hexane) provided 3.60 g (14.6 mmol, 80%) of the enoate (14).

3-(3-Chloro-benzo[b]thiophen-2-yl)-propionic acid methyl ester (15). A solution of 3.60 g (14.6 mmol) of 14 in 50 mL THF was treated with Wilkinson's catalyst (3.35 g, 3.62 mmol). The mixture was stirred under 1 atm $H_2$ for 18 h and then was filtered through celite. The solvent was evaporated and the residue purified by flash chromatography on silica gel (0–2% ethyl acetate/hexane) to give 3.63 g (14.3 mmol, 99%) of the saturated ester (15).

3-(3-Chloro-benzo[b]thiophen-2-yl)-propan-1-ol (16). An ice cold solution of 3.63 g (14.3 mmol) of 15 in 60 mL of ether was treated with $LiBH_4$ (621 mg, 28.5 mmol) and methanol (2 mL). After 30 min., 30 mL of 0.5 M NaOH solution was added. The mixture was extracted with ethyl acetate (2×25 mL) and the combined ethyl acetate solution washed with brine (50 mL), dried ($MgSO_4$), filtered and evaporated. The residue was purified by flash chromatography on silica gel (5–20% ethyl acetate/hexane) to give 2.57 g (11.3 mmol, 79%) of the alcohol (16).

3-(3-Chloro-benzo[b]thiophen-2-yl)-propionaldehyde (17). A −78° C. solution of oxalyl chloride (1.73 g, 13.6 mmol) in dichloromethane (20 mL) was treated with DMSO (20 mL). After 5 min., a solution of alcohol 16 (2.57 g, 11.3 mmol) in dichloromethane (20 mL) was added. After another 15 min., triethylamine (7.1 mL, 50.6 mmol) was added. The reaction was stirred at −78° C. for 5 min., and then allowed to warm to room temperature. After 30 min., 100 mL water was added and the mixture extracted with dichloromethane (3×60 mL). The combined dichloromethane solution was dried ($Na_2SO_4$), filtered and evaporated. Purification by flash chromatography on silica gel (10% ethyl acetate/hexane) gave 2.11 g (9.4 mmol, 83%) of the aldehyde (17).

5-(3-Chloro-benzo[b]thiophen-2-yl)-pent-1-yn-3-ol (18). A solution of aldehyde 17 (2.11 g, 9.4 mmol) in 15 mL THF was added to a solution of ethynylmagnesium bromide (28.2 mL, 14.1 mmol, 0.5 M THF) at 0° C. After 1.5 h, saturated $NH_4Cl$ solution (75 mL) was added and the mixture was extracted with ethyl acetate (3×50 mL). The combined ethyl acetate solution was washed with brine (50 mL) and then was dried ($Na_2SO_4$), filtered and evaporated: Purification by flash chromatography (5–20% ethyl acetate/hexane) gave 2.20 g (8.78 mmol, 93%) of the alcohol (18).

tert-Butyl-{1-[2-(3-chloro-benzo[b]thiophen-2-yl)ethyl]-prop-2-ynyloxy}-dimethyl-silane (19). A solution of alcohol 18 (2.20 g, 8.78 mmol) in dichloromethane (15 mL) was treated with DMAP (215 mg, 1.8 mmol), TBSCl (1.59 g, 10.5 mmol), and triethylamine (1.8 mL, 13.2 mmol). The reaction was stirred for 24 h and then saturated sodium bicarbonate solution (50 mL) was added. The mixture was extracted with dichloromethane (2×50 mL) and the combined dichloromethane solution dried ($Na_2SO_4$), filtered and evaporated. Purification by flash chromatography (4% ethyl acetate/hexane) gave 3.06 g (6.4 mmol, 73%) of the protected alcohol (19).

(3-{(1R,4S,5S)-4-(tert-Butyl-dimethyl-silanyloxy)-5-[(E)-3-(tert-butyl-dimethyl-silanyloxy)-5-(3-chloro-benzo[b]thiophen-2-yl)-pent-1-enyl]-3,3-dimethyl-2-oxo-cyclopentylsulfanyl}-propylsulfanyl)-acetic acid methyl ester (20). A solution of alkyne 19 (105 mg, 0.28 mmol) in THF (1.2 mL) was treated with bis(cyclopentadienyl) zirconium chloride hydride (91 mg, 0.35 mmol). The reaction was stirred for 30 min., then was cooled to –78° C. and treated with methyllithium (0.46 mL, 0.64 mmol, 1.4 M in ether). After 10 min., a precooled (–78° C.) solution of lithium 2-thienylcyanocuprate (1.3 mL, 0.33 mmol, 0.25 M in THF) was added by cannula. The reaction was stirred for 45 min. and then enone 10 (61 mg, 0.15 mmol) in 0.2 mL THF was added by cannula, rinsing with 0.2 mL THF. After 1 h, The reaction was quenched by addition of 20 mL 1:1 saturated ammonium chloride solution/concentrated ammonium hydroxide. The mixture was stirred for 45 min. and then was extracted with ethyl acetate (3×20 mL). The combined ethyl acetate solution was dried ($Na_2SO_4$), filtered and evaporated. Purification by flash chromatography on silica gel (10% ethyl acetate/hexanes) gave 51 mg (0.064 mmol, 43%) of the coupled product (20).

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid methyl ester (21, 22). A solution of 20 (51 mg, 0.064 mmol) in $CH_3CN$ (1.6 mL) was treated with HF-pyridine (0.26 mL). The reaction was stirred for 24 h and then was quenched by addition of 15 mL saturated sodium bicarbonate solution. The mixture was extracted with dichloromethane (3×10 mL) and the combined dichloromethane solution was dried ($Na_2SO_4$), filtered and evaporated. Purification by preparative thin layer chromatography on silica gel (40% ethyl acetate/hexanes) gave 12 mg (0.023 mmol, 71%) of each diastereomer.

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid (23, 24). Rabbit liver esterase (9 mg) was added to a solution of the lower $R_f$ ester 21 (11 mg, 0.021 mmol) in pH 7.2 phosphate buffer (0.5 mL)/$CH_3CN$ (0.1 mL). The mixture was stirred overnight and then 10 mL 0.5 M HCl was added along with a few mL's of brine. The mixture was extracted with ethyl acetate (3×10 mL) and the combined ethyl acetate solution dried ($Na_2SO_4$), filtered and evaporated. Purification by flash chromatography on silica gel (3–5% MeOH/$CH_2Cl_2$) gave 4 mg (0.0078 mmol, 37%) of the acid (23). 300 MHz $^1$H NMR ($CDCl_3$, ppm) δ 7.73 (2H, d, J=8.4 Hz) 7.4–7.3 (2H, m) 5.9–5.8 (1H, m) 5.8–5.7 (1H, m) 4.4–4.3 (1H, m) 3.63 (1H, d, J=9.7 Hz) 3.21 (2H, s) 3.1–2.4 (11H, overlapping m) 2.1–1.7 (4H, overlapping m) 1.12 (3H, s) 1.03 (3H, s).

The higher $R_f$ ester was hydrolyzed similarly except a solution of rabbit liver esterase (10 mg) in 0.5 mL of pH 7.2 phosphate buffer was added to a solution of the ester (10 mg, 0.019 mmol) in $CH_3CN$ (0.2 mL). The reaction was stirred for 22 h and then worked up and purified as above. This gave 7 mg (0.013 mmol, 71%) of the acid (24). 300 MHz $^1$H NMR ($CDCl_3$, ppm) δ 7.73 (2H, d, J=8.8 Hz) 7.44–7.31 (2H, m) 5.9–5.8 (1H, m) 5.8–5.7 (1H, m) 4.4–4.3 (1H, m) 3.64 (1H, d, J=9.7 Hz) 3.3–2.3 (13H, overlapping m) 2.1–1.7 (4H, overlapping m) 1.12 (3H, s) 1.03 (3H, s).

tert-Butyl-hex-5-ynyloxy-dimethyl-silane (26).

7-(tert-Butyl-dimethyl-silanyloxy)-hept-2-yn-1-ol (27).

Acetic acid 7-(tert-butyl-dimethyl-silanyloxy)-hept-2-ynyl ester (28). A solution of 7-(tert-Butyl-dimethyl-silanyloxy)-hept-2-yn-1-ol 27 (4.507 g, 21 mmol) in pyridine (20 mL) was treated with acetic anhydride (3.0 mL, 31.8 mmol). After 18 h, the solvent was evaporated and the residue co-evaporated with toluene. The residue was used directly in the next step.

7-Acetoxy-hept-5-ynoic acid (29). A solution of crude 28 in acetone (100 mL) was treated with Jones Reagent (18.0 mL, 41.4 mmol, 2.3 M). The mixture became warm and so was cooled with an ice bath. After 1 h at room temperature, 10 mL isopropyl alcohol was added and the mixture stirred further for 15 min. The mixture still had a brown color so another 10 mL isopropyl alcohol was added. After another 15 min., the color had not changed so the mixture was filtered through celite and the filtrate evaporated in vacuo. The residue was partitioned between 100 mL ether and 100 mL saturated ammonium chloride solution. The aqueous layer was extracted with 100 mL ether and the combined ether solution washed with brine and then was dried ($MgSO_4$), filtered and evaporated to leave a yellow oil (6.333 g) that was used directly in the next step.

7-Hydroxy-hept-5-ynoic acid methyl ester (30). The crude acid 29 (6.333 g) was treated with a 1% solution of acetyl chloride in methanol (60 mL). After 16 h, sodium bicarbonate (1.966 g, 23.4 mmol) was added. The mixture was dried ($MgSO_4$), filtered through celite and evaporated in vacuo. Purification by flash chromatography on silica gel (30–40% ethyl acetate/hexanes) gave 7-Hydroxy-hept-5-ynoic acid methyl ester 30 (3.022 g, 19.3 mmol, 92% from 7-tert-Butyl-dimethyl-silanyloxy)-hept-2-yn-1-ol 27).

7-Iodo-hept-5-ynoic acid methyl ester (31). A solution of 30 (1.347 g, 8.6 mmol) in 5 mL dichloromethane was added to a mixture of triphenylphosphine (2.725 g, 10.4 mmol), imidazole (726 mg, 10.7 mmol), and iodine (2.602 g, 10.3 mmol) in 34 mL dichloromethane, rinsing with 5 mL dichloromethane. After 40 min., the dichloromethane was evaporated in vacuo to a few mL's and the resulting mixture filtered through basic alumina, washing with 10% ethyl acetate/hexanes. Purification by flash chromatography on silica gel (10% ethyl acetate/hexanes) gave 1.878 g (7.1 mmol, 83%) of the propargyl iodide.

tert-Butyl-{(E)-1-[2-(3-chloro-benzo[b]thiophen-2-yl)-ethyl]-3-iodo-allyloxy}-dimethyl-silane (32). A solution of alkyne 19 (5.547 g, 15.2 mmol) in dichloromethane (50 mL) was treated with $Cp_2ZrHCl$ (5.794 g, 22.5 mmol). The reaction was stirred for 45 min. and then N-iodosuccinimide (4.966 g, 22.1 mmol) was added. After 15 min., saturated sodium bicarbonate solution (200 mL) was added and the mixture was extracted with dichloromethane (2×100 mL). The combined dichloromethane solution was dried ($MgSO_4$), filtered and evaporated. Purification by flash chromatography on silica gel (0–5% ethyl acetate/hexanes) gave 6.608 g (13.1 mmol, 86%) of the vinyl iodide (32).

7-{(1R,4S,5R)-4-(tert-Butyl-dimethyl-silanyloxy)-5-[(E)-3-(tert-butyl-dimethyl-silanyloxy)-5-(3-chloro-benzo[b]thiophen-2-yl)-pent-1-enyl]-3,3-dimethyl-2-oxo-cyclopentyl}-hept-5-ynoic acid methyl ester (33). A –78° C. solution of iodide 32 (675 mg, 1.34 mmol) in THF (2.0 mL) was treated with tert-butyllithium (1.73 mL, 2.94 mL, 1.7 M/pentane). The dark red mixture was stirred for 25 min. and then dimethylzinc (0.80 mL, 1.6 mmol, 2 M/toluene)

was added. The solution was stirred at 0° C. for 15 min. and then recooled to −78° C. At this time, a solution of enone 6 (208 mg, 0.87 mmol) in THF (1.0 mL) was added over 2 h by syringe pump, rinsing with 0.5 mL THF. After 30 min., HMPA (1.34 mL, distilled from CaH$_2$) was added followed by a solution of propargyl iodide 31 (1.286 g, 4.83 mmol) in THF (1.0 mL). The solution was stirred in a −40° C. bath overnight and then 20 mL saturated ammonium chloride solution and 10 mL water were added. The mixture was extracted with dichloromethane (20 mL) and ethyl acetate (2×20 mL). The combined organic extracts were dried (MgSO$_4$), filtered and evaporated. Purification by flash chromatography on silica gel (5–10% ethyl acetate/hexanes) gave 198 mg (0.27 mmol, 31%) of 33.

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid methyl ester (34, 35). A solution of 33 (198 mg, 0.27 mmol) in CH$_3$CN (6.5 mL) was treated with HF-pyridine (1.2 mL). The solution was stirred for 3 h and saturated sodium bicarbonate solution (120 mL) was added. The mixture was extracted with dichloromethane (3×50 mL) and the combined dichloromethane solution dried (Na$_2$SO$_4$), filtered and evaporated. Purification by flash chromatography (50% ethyl acetate/hexane) followed by preparative TLC (55% ethyl acetate/hexane) gave 55 mg (0.11 mmol, 41%) of the less polar diastereomer (34) and 51 mg (0.10 mmol, 37%) of the more polar diastereomer (35).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid (low R$_f$ diastereomer, 36). A solution of 34 (9 mg, 0.017 mmol) and rabbit liver esterase (1 mg) in pH 7.2 phosphate buffer (2 mL)/CH$_3$CN (0.1 mL) was stirred for 17 h. The mixture was then coevaporated with CH$_3$CN to remove water and the residue purified by flash chromatography on silica gel (3–7% MeOH/CH$_2$Cl$_2$) to give 8 mg (0.016 mmol, 93%) of the acid (36).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid (high R$_f$ diastereomer, 37). A solution of 35 (12 mg, 0.023 mmol) and rabbit liver esterase (1 mg) in pH 7.2 phosphate buffer (2 mL)/CH$_3$CN (0.1 mL) was stirred for 17 h. TLC showed the presence of starting material, so another 2 mg of the esterase was added. After stirring for another 24 h, the reaction was complete. Work up and purification as above for 36 gave 8 mg (0.016 mmol, 69%) of the acid (37).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (low R$_f$ diastereomer, 38). Ethanol (95%, 2.5 mL) was added to NiCl$_2$ (50 mg, 0.39 mmol) and NaBH$_4$ (7 mg, 0.19 mmol). The resulting black mixture was stirred for 5 min. and then ethylenediamine (41 µL, 0.61 mmol) was added. After 15 min., a solution of alkyne 34 (40 mg, 0.077 mmol) in 0.5 mL 95% ethanol was added, rinsing with 0.5 mL ethanol. The flask was purged with H$_2$ and allowed to stir under 1 atm H$_2$ for 22 h. The mixture was then filtered through celite and purified by flash chromatography on silica gel (55% ethyl acetate/hexanes) to give 17 mg (0.032 mmol, 43%) of the alkene (38).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester (high R$_f$ diastereomer 39). The same procedure as for 36 was followed to give 17 mg (0.032 mmol, 41%) of 39.

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid (low R$_f$ diastereomer, 40). The same procedure as above for 36 was used to give 9 mg (0.018 mmol, 85%) of acid 40. 300 MHz $^1$H NMR (CDCl$_3$, ppm) δ 7.73 (2H, d, J=8.4 Hz) 7.45–7.30 (2H, m) 5.8–5.6 (2H, m) 5.4–5.3 (2H, m) 4.3–4.1 (1H, m) 3.57 (1H, d, J=9.7 Hz) 3.1–2.9 (2H, m) 2.5–1.9 (10H, m) 1.7–1.6 (2H, m) 1.09 (3H, s) 0.89 (3H, s).

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid (high R$_f$ diastereomer, 41). The same procedure as above for the 36 was used to give 9 mg (0.018 mmol, 85%) of acid 41. 300 MHz $^1$H NMR (CDCl$_3$, ppm) δ 7.73 (2H, d, J=8.8 Hz) 7.45–7.30 (2H, m) 5.8–5.6 (2H, m) 5.45–5.30 (2H, m) 4.3–4.2 (1H, m) 3.61 (1H, d, J=9.7 Hz) 3.1–3.0 (2H, m) 2.5–1.9 (10H, m) 1.7–1.6 (2H, m) 1.10 (3H, s) 0.90 (3H, s).

The methods of screening the compounds of this invention for the desired biological activity are illustrated in the following non-limiting examples. Results for example compounds of this invention are included in Table 2. These results are presented purely for illustrative purposes and are not intended to limit the scope of the invention in any way.

Radioligand Binding

Cells Stably Expressing EP$_1$, EP$_2$, EP$_4$ and FP Receptors

HEK-293 cells stably expressing the human or feline FP receptor, or EP$_1$, EP$_2$, or EP$_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM MgCl$_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl PGF$_{2α}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] PGE$_2$ (specific activity 180 Ci mmol) was used as the radioligand for EP receptors. [$^3$H] 17-phenyl PGF$_{2α}$ was employed for FP receptor binding studies. Binding studies employing EP$_1$, EP$_2$, EP$_4$ and FP receptors were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-PGE$_2$, or 5 nM [$^3$H] 17-phenyl PGF$_{2α}$ and non-specific binding determined with 10$^{-5}$M of unlabeled PGE$_2$, or 17-phenyl PGF$_{2α}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3A}$/Gqi5; hEP$_4$/Gqs5; hFP; hIP; hTP), were cultured in 100 mm culture dishes in high-glucose DMEM medium containing 10% fetal bovine serum, 2 mM 1-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the FLIPR™

Cells were seeded at a density of 5×10$^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates were washed four times with HBSS-HEPES buffer to remove excess dye leaving 100 µl in each well. Plates were re-equilibrated to 37° C. for a few minutes.

Cells were excited with an Argon laser at 488 nm, and emission was measured through a 510–570 nm bandwidth emission filter (FLIPR™, Molecular Devices, Sunnyvale, Calif.). Drug solution was added in a 50 µl volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_{3A}$/Gqi5; hEP$_4$/Gqs5); PGF$_{2\alpha}$ (hFP); carbacyclin (hIP); U-46619 (hTP), depending on receptor). The peak fluorescence change in each drug-containing well was then expressed relative to the controls.

Compounds were tested in a high-throughput (ETS) or concentration-response (CoRe) format. In the HTS format, forty-four compounds per plate were examined in duplicates at a concentration of 10$^{-5}$ M. To generate concentration-response curves, four compounds per plate were tested in duplicates in a concentration range between 10$^{-5}$ and 10$^{-11}$ M. The duplicate values were averaged. In either, HTS or CoRe format each compound was tested on at least 3 separate plates using cells from different passages to give an n≧3.

TABLE 2

| Compound | hFP | hEP$_1$ | hEP$_2$ | hEP$_{3D}$/hEP$_{3A}$ | hEP$_4$ | hDP | hIP | hTP |
|---|---|---|---|---|---|---|---|---|
| 21 | NA | NA | >10K | NA | 98 | NA | NA | NA |
| 22 | | | NA | NA | 300 | | | |
|  | NA | NA | NA | NA | 30 | NA | NA | NA |
| 23 | | | NA | >10K | 44 | | | |
|  | NA | NA | NA | NA | 0.1 | NA | NA | >10K |
| 24 | | | NA | >>10K | 26 | | | |
|  | NA | NA | NA | NA | 0.1 | NA | NA | NA |
| 34 | | | NA | | >10K | | | |
|  | NA | | | NA | >10K | | NA | NA |
| 35 | NA | | | NA | 2455 | | NA | NA |
| 36 | | | NA | | 200 | | | |
|  | NA | | | NA | 66 | | >10K | NA |
| 37 | | | NA | | 100 | | | |
|  | NA | | | NA | 32 | | >10K | NA |
| 38 | | | NA | | 2700 | | | |
|  | NA | | | NA | 269 | | NA | NA |
| 39 | | | NA | | 2300 | | | |
|  | NA | | | NA | 141 | | NA | NA |

TABLE 2-continued

| Compound | hFP | hEP$_1$ | hEP$_2$ | hEP$_{3D}$/hEP$_{3A}$ | hEP$_4$ | hDP | hIP | hTP |
|---|---|---|---|---|---|---|---|---|
| 40 | | | NA | | 200 | | | |
|  | NA | | | NA | 0.3 | | NA | >10K |
| 41 | | | >10K | | 20 | | | |
|  | NA | | | NA | | | NA | >10K |
| 42 | | | NA | >10$^4$ | >10$^4$ | | | |
|  | NA | NA | NA | 559 | NA | NA | NA | NA |
| 43 | | | NA | 1700 | 400 | | | |
|  | NA | >10$^4$ | NA | 11 | 63 | | 3981 | 18 |
| 44 | | | 1500 | 300 | 5.5 | | | |
|  | NA | 782 | 944 | 4.6 | 0.2 | >10K | 284 | 18 |
| 45 | | | NA | >10$^4$ | 400 | | NA | 631 |
|  | NA | NA | NA | 531 | 51 | NA | NA | NA |
| 46 | | | >10K | >10K | 4 | | | |
|  | NA | 290 | | 589 | 0.4 | NA | NA | |
| 47 | | | NA | | 76 | | | |
|  | NA | 963 | | >10K | | | NA | |
| 48 | | | NA | | 45 | | | |
| 49 | | | NA | | 1400 | | | |
| 50 | | | NA | 6607 | 2400 | | | |
|  | NA | 638 | | >10K | 3162 | | NA | >10K |
| 51 | | | NA | NA | 700 | | NA | |
| 52 | | | NA | | 72 | | | |
|  | NA | 27 | | 60 | 18 | | NA | |
| 53 | | | | | 59 | | | |
|  | NA | 1020 | NA | 1862 | 6.4 | | NA | |

The top numbers are the radioligand bindng values(nm)
The botttom numbers are the functional data (nm)

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension or glaucoma which comprises administering to an animal having ocular hypertension or glaucoma a therapeutically effective amount of a compound represented by the general Formula I:

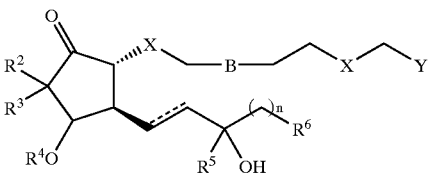

Formula I wherein the dashed lines indicate the presence or absence of a bond, the hatched wedges indicate the α (down) configuration, and the solid triangles indicate the β (up) configuration;

B is a single, double, or triple covalent bond;

n is 0–6;

X is CH$_2$, S or O;

Y is any pharmaceutically acceptable salt of $CO_2H$, or $CO_2R$, $CONR_2$, $NHCH_2CH_2OH$, $N(CH_2CH_2OH)_2$, $CH_2OR$, $P(O)(OR)_2$, $CONRSO_2R$, $SONR_2$, or

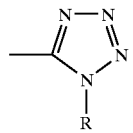

R is H, $C_{1-6}$ alkyl or $C_{2-6}$ alkenyl;

$R^2$ and $R^3$ are $C_{1-6}$ linear alkyl which may be the same or different, and may be bonded to each other such that they form a ring incorporating the carbon to which they are commonly attached;

$R^4$ is hydrogen, R, C(=O)R, or any group that is easily removed under physiological conditions such that $R^4$ is effectively hydrogen;

$R^5$ is hydrogen or R; and $R^6$ is
i) hydrogen;
ii) a linear or branched hydrocarbon containing between 1 and 8 carbon atoms, which may contain one or more double or triple bonds, or oxygen or halogen derivatives of said hydrocarbon, wherein 1–3 carbon or hydrogen atoms may be substituted by O or a halogen; or
iii) aryloxy, heteroaryloxy, $C_{3-8}$ cycloalkyloxy, $C_{3-8}$ cycloalkyl, $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{6-10}$ aryl, $C_{3-10}$ heteroaryl, aryloxy, heteroaryloxy, $C_{1-6}$ alkyl, OR, SR, and $SO_2R$.

2. The method of claim 1 wherein the compound of Formula I is not a compound of Formula II

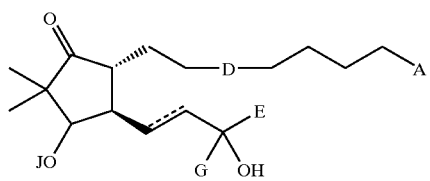

Formula II wherein

A is $CO_2H$ or $CO_2Me$;

D is a single, double, or triple covalent bond;

E is a linear, branched, or cycloalkyl chain of 3 to 7 carbons, trifluoromethylbutyl, hydroxyalkyl, or $CH_2R^7$ wherein $R^7$ is phenyl, cyclopentyl, phenoxy, chlorophenoxy, propoxy, or —$CH_2SCH_2CH_3$;

J is hydrogen, R, C(=O)R, or any group that is easily removed under physiological conditions such that $R^4$ is effectively hydrogen; and G is H or $CH_3$.

3. The method of claim 2 wherein the compound of Formula I is further represented by Formula III

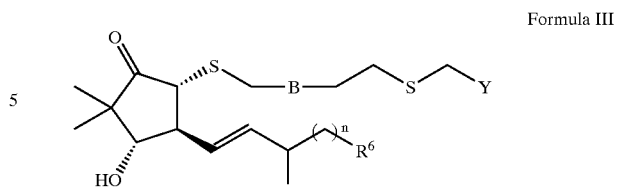

Formula III wherein Y is $CO_2R$, or any pharmaceutically acceptable salt of $CO_2H$.

4. The method of claim 3 wherein $R^6$ is $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{1-6}$ alkyl, OR, SR, and $SO_2R$.

5. The method of claim 4 wherein $R^6$ is napthyl, benzofuranyl, or benzothienyl, which may contain one or more substituents selected from the group consisting of halogen, trihalomethyl, cyano, nitro, amino, hydroxy, $C_{1-6}$ alkyl, OR, SR, and $SO_2R$.

6. The method of claim 5 wherein Y is $CO_2H$ or $CO_2Me$.

7. The method of claim 6 wherein $R^6$ is 3-chlorobenzothien-2-yl.

8. The method of claim 7 wherein n is 2.

9. The method of claim 8 wherein B is a single bond.

10. The method of claim 2 wherein the compound of Formula I is further represented by Formula IV

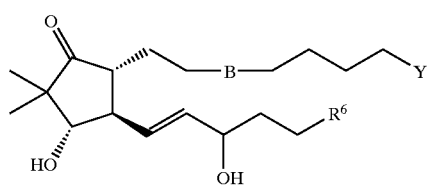

Formula IV wherein

Y is $CO_2R$, or any pharmaceutically acceptable salt of $CO_2H$; and $R^6$ is $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{1-6}$ alkyl, OR, SR, and $SO_2R$.

11. The method of claim 10 wherein Y is $CO_2H$ or $CO_2Me$.

12. The method of claim 11 wherein $R^6$ is phenyl.

13. The method of claim 12 wherein B is a double bond.

14. The method of claim 11 wherein $R^6$ is napthyl, benzofuranyl, or benzothienyl, which may contain one or more substituents selected from the group consisting of halogen, trihalomethyl, cyano, nitro, amino, hydroxy, $C_{1-6}$ alkyl, OR, SR, and $SO_2R$.

15. The method of claim 14 wherein $R^6$ is 3-chlorobenzothien-2-yl.

16. The method of claim 15 wherein B is a double or triple bond.

17. The method of claim 1 wherein said compound is selected from the group consisting of:

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid methyl ester;

(3-{(1R,4S,5S)-5-(3-chloro-benzo[b]thiophen-2-yl)-3-hydroxy-pent-1-enyl]-4-hydroxy-3,3-dimethyl-2-oxo-cyclopentylsulfanyl}-propylsulfanyl)-acetic acid;

(Z)-7-{(1R,4S,5R)-5-[(E)-5-(3-chloro-benzo[b]thiophene-2-yl)-3-hydroxy-pent-1enyl]-4-hydroxy-3,3-dimethyl-2-oxo-cyclopentyl}-hept-5-ynoic acid methyl ester;

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-ynoic acid;

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid methyl ester;

(Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid;

7-[(1R,4S,5R)-4-Hydroxy-5-((E)-(S)-3-hydroxy-oct-1-enyl)-3,3-dimethyl-2-oxo-cyclopentyl]-hept-5-ynoic acid methyl ester;

7-[(1R,4S,5R)-4-Hydroxy-5-((E)-(S)-3-hydroxy-oct-1-enyl)-3,3-dimethyl-2-oxo-cyclopentyl]-hept-5-ynoic acid;

(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid;

(Z)-7-[(1R,4S,5R)-4-Hydroxy-5-((E)-(S)-3-hydroxy-oct-1-enyl)-3,3-dimethyl-2-oxo-cyclopentyl]-hept-5-enoic acid methyl ester;

(Z)-7-[(1R,4S,5R)-4-Hydroxy-5-((E)-3-hydroxy-4-phenyl-but-1-enyl)-3,3-dimethyl-2-oxo-cyclopentyl]-hept-5-enoic acid;

(Z)-7-[(1R,4S,5R)-4-Hydroxy-5-((E)-3-hydroxy-4-phenyl-but-1-enyl)-3,3-dimethyl-2-oxo-cyclopentyl]-hept-5-enoic acid methyl ester;

(Z)-7-[(1R,4S,5R)-4-Hydroxy-5-((E)-3-hydroxy-5-phenyl-pent-1-enyl)-3,3-dimethyl-2-oxo-cyclopentyl]-hept-5-enoic acid methyl ester;

(Z)-7-[(1R,4S,5R)-4-Hydroxy-5-((E)-3-hydroxy-5-phenyl-pent-1-enyl)-3,3-dimethyl-2-oxo-cyclopentyl]-hept-5-enoic acid;

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid;

7-[(1R,4S,5R)-5-((E)-4-Benzo[b]thiophen-2-yl-3-hydroxy-but-1-enyl)-4-hydroxy-3,3-dimethyl-2-oxo-cyclopentyl]-heptanoic acid;

(Z)-7-[(1R,4S,5R)-5-(4-Benzo[b]thiophen-2-yl-3-hydroxy-butyl)-4-hydroxy-3,3-dimethyl-2-oxo-cyclopentyl]-hept-5-enoic acid;

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid ethylamide;

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid diethylamide;

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (2-hydroxy-ethyl)-amide; and (3S,4R,5R)-4-((E)-4-Benzo[b]thiophen-2-yl-3-hydroxy-but-1-enyl)-3-hydroxy-2,2-dimethyl-5-[(Z)-6-(1-H-tetrazol-5-yl)-hex-2-enyl]-cyclopentanone.

18. An ophthalmic solution comprising a therapeutically effective amount of a compound represented by the general Formula 1

Formula I

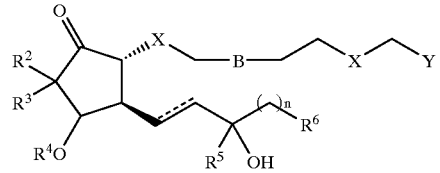

wherein the dashed lines indicate the presence or absence of a bond, the hatched wedges indicate the α (down) configuration, and the solid triangles indicate the β (up) configuration;

B is a single, double, or triple covalent bond;

n is 0–6;

X is $CH_2$, S or O;

Y is any pharmaceutically acceptable salt of $CO_2H$, or $CO_2R$, $CONR_2$, $NHCH_2CH_2OH$, $N(CH_2CH_2OH)_2$, $CH_2OR$, $P(O)(OR)_2$, $CONRSO_2R$, $SONR_2$, or

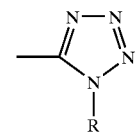

R is H, $C_{1-6}$ alkyl or $C_{2-6}$ alkenyl;

$R^2$ and $R^3$ are $C_{1-6}$ linear alkyl which may be the same or different, and may be bonded to each other such that they form a ring incorporating the carbon to which they are commonly attached;

$R^4$ is hydrogen, R, C(=O)R, or any group that is easily removed under physiological conditions such that $R^4$ is effectively hydrogen;

$R^5$ is hydrogen or R; and $R^6$ is i) hydrogen;

ii) a linear or branched hydrocarbon containing between 1 and 8 carbon atoms, which may contain one or more double or triple bonds, or oxygen or halogen derivatives of said hydrocarbon, wherein 1–3 carbon or hydrogen atoms may be substituted by O or a halogen; or iii) aryloxy, heteroaryloxy, $C_{3-8}$ cycloalkyloxy, $C_{3-8}$ cycloalkyl, $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{6-10}$ aryl, $C_{3-10}$ heteroaryl, aryloxy, heteroaryloxy, $C_{1-6}$ alkyl, OR, SR, and $SO_2R$.

19. A pharmaceutical product, comprising a container adapted to dispense the contents of said container in metered form; and an ophthalmic solution according to claim 18 in said container.

20. The method of making compounds of Formula V

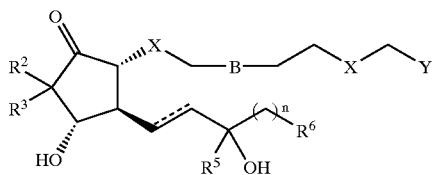

Formula V wherein part of the synthesis comprises reducing a compound of Formula VI to a compound of Formula VII in the presence of Baker's yeast

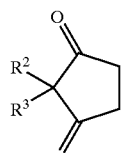

Formula VI

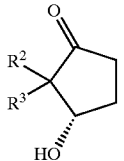

Formula VII wherein the dashed lines indicate the presence or absence of a bond, the hatched wedges indicate the α (down) configuration, and the solid triangles indicate the β (up) configuration;

B is a single, double, or triple covalent bond;
n is 0–6;
X is $CH_2$, S or O;
Y is any pharmaceutically acceptable salt of $CO_2H$, $CO_2R$, $CONR_2$, $NHCH_2CH_2OH$, $N(CH_2CH_2OH)_2$, $CH_2OR$, $P(O)(OR)_2$, $CONRSO_2R$, $SONR_2$, or

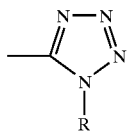

R is H, $C_{1-6}$ alkyl or $C_{2-6}$ alkenyl;
$R^2$ and $R^3$ are $C_{1-6}$ linear alkyl which may be the same or different, and may be bonded to each other such that they form a ring incorporating the carbon to which they are commonly attached;
$R^5$ is hydrogen or R; and
$R^6$ is
  i) hydrogen;
  ii) a linear or branched hydrocarbon containing between 1 and 8 carbon atoms, which may contain one or more double or triple bonds, or oxygen or halogen derivatives of said hydrocarbon, wherein 1–3 carbon or hydrogen atoms may be substituted by O or a halogen; or
  iii) aryloxy, heteroaryloxy, $C_{3-8}$ cycloalkyloxy, $C_{3-8}$ cycloalkyl, $C_{6-10}$ aryl or $C_{3-10}$ heteroaryl, wherein one or more carbons is substituted with N, O, or S; and which may contain one or more substituents selected from the group consisting of halogen, trihalomethyl, cyano, nitro, amino, hydroxy, $C_{6-10}$ aryl, $C_{3-10}$ heteroaryl, aryloxy, heteroaryloxy, $C_{1-6}$ alkyl, OR, SR, and $SO_2R$.

21. The method of making compounds of Formula VIII comprising:

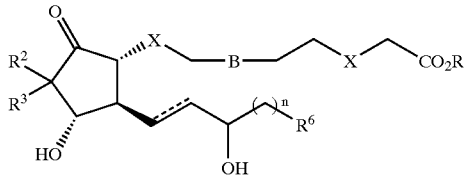

Formula VIII i) reacting a compound of Formula IX with a compound of Formula X in the presence of a suitable base to form a compound of Formula XI;

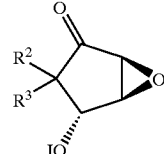

Formula IX

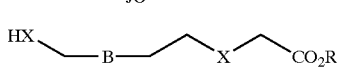

Formula X

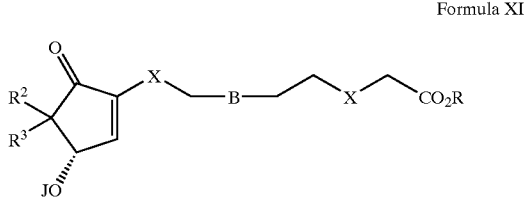

Formula XI ii) coupling a compound of Formula XI with a compound of Formula XII; and

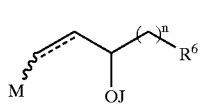

Formula XII iii) removing the protecting groups and separating the diastereomers to obtain the desired products;
wherein the hatched wedges indicate the α (down) configuration, the solid triangles indicate the β (up) configuration, and the wavy lines indicate either the cis (Z) or trans (Z) conformation;
n is 0–6;
B is a single, double, or triple covalent bond;
J is a protecting group that can be easily removed to form the respective hydroxide group without affecting the rest of the molecule;
R is $C_{1-6}$ alkyl or $C_{2-6}$ alkenyl;
$R^2$ and $R^3$ are $C_{1-6}$ linear alkyl which may be the same or different, and may be bonded to each other such that they form a ring incorporating the carbon to which they are commonly attached;
X is S or O wherein both X moieties are identical; and
M is a group that comprises one or more metal atoms.

22. The method of claim 1 wherein the compound of Formula I which is further represented by Formula XIII Formula XIII

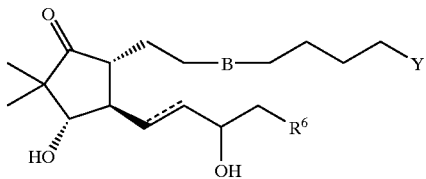

wherein B represents a single or double bond;

and $R^6$ is napthyl, benzofuranyl, or benzothienyl, which may contain one or more substituents selected from the group consisting of halogen, trihalomethyl, cyano, nitro, amino, hydroxy, $C_{1-6}$ alkyl, OR, SR, and $SO_2R$.

23. The method of claim 22 wherein $R^6$ is benzothien-2-yl.

24. The method of claim 23 wherein Y is any pharmaceutically acceptable salt of $CO_2H$, or $CO_2R$, $CONR_2$, $NHCH_2CH_2OH$, $N(CH_2CH_2OH)_2$, or

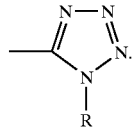

25. The method of claim 24 wherein the dashed line indicates the presence of a bond and B is a double bond.

26. The method of claim 24 wherein the dashed line indicates the presence of a bond and B is a single bond.

27. The method of claim 24 wherein the dashed line indicates the absence of a bond and B is a double bond.

* * * * *

UNITED STATES PATENT AND TRADEMARK OFFICE
CERTIFICATE OF CORRECTION

PATENT NO. : 6,875,787 B2 Page 1 of 8
APPLICATION NO. : 10/365369
DATED : April 5, 2005
INVENTOR(S) : Donde It is certified that error appears in the above-identified patent and that said Letters Patent is hereby corrected as shown below:

On the Title Page, Item -56- under "Other Publications", in column 1, line 3, delete "1036–10–39." and insert -- 1036–1039. --, therefor.

On the Title Page, Item -56- under "Other Publications", in column 1, line 15, delete "uveoscieral" and insert -- uveoscleral --, therefor.

In column 2, line 21, delete "(see," and insert -- see, --, therefor.

In column 13, line 1, delete " 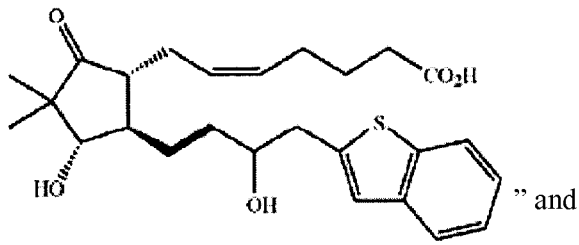 " and insert -- 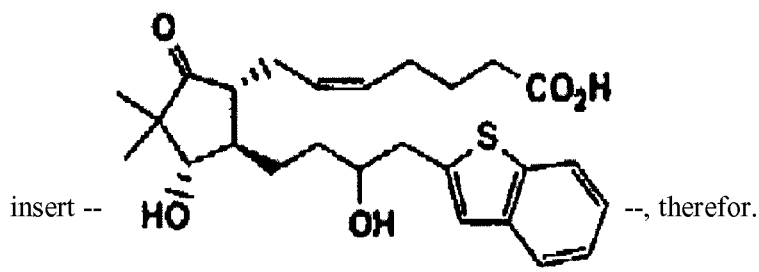 --, therefor.

In column 13, line 5, delete " 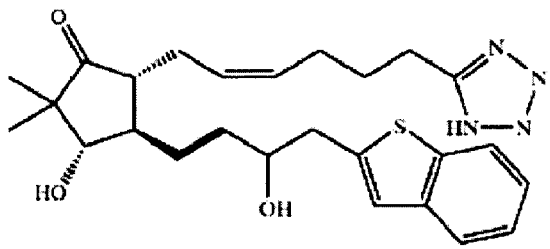 " and insert -- 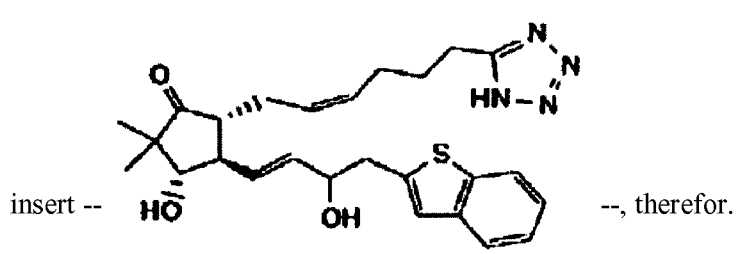 --, therefor.

UNITED STATES PATENT AND TRADEMARK OFFICE
CERTIFICATE OF CORRECTION

PATENT NO. : 6,875,787 B2  
APPLICATION NO. : 10/365369  
DATED : April 5, 2005  
INVENTOR(S) : Donde Page 2 of 8

It is certified that error appears in the above-identified patent and that said Letters Patent is hereby corrected as shown below:

In column 15, line 35, delete "cyclopentyl)" and insert -- cyclopentyl] --, therefor.

In column 18, line 47, delete "mmol;" and insert -- mmol, --, therefor.

In column 18, line 58, delete "8.0 ml," and insert -- 8.0 mL, --, therefor.

In column 20, line 60, delete "evaporated:" and insert -- evaporated. --, therefor.

In column 20, line 63, delete "2-yl)ethyl]" and insert -- 2-yl)-ethyl] --, therefor.

In column 21, line 21, after "1 h," delete "The" and insert -- the --, therefor.

In column 22, line 35, delete "7-tert" and insert -- 7-(tert --, therefor.

In column 22, line 35, delete "27)." and insert -- (27). --, therefor.

In column 25, line 32, delete "(hEP$_1$;" and insert -- (hEP$_1$); --, therefor.

In column 25, line 37, delete "(ETS)" and insert -- (HTS) --, therefor.

In column 26, line 27, delete "bindng" and insert -- binding --, therefor.

In column 26, line 28, delete "botttom" and insert -- bottom --, therefor.

In column 29, line 5, in Claim 17, delete "pent-1enyl]" and insert -- pent-1-enyl] --, therefor.

In column 30, line 3, in Claim 18, delete "Formula 1" and insert -- Formula I --, therefor.

In table 1, delete

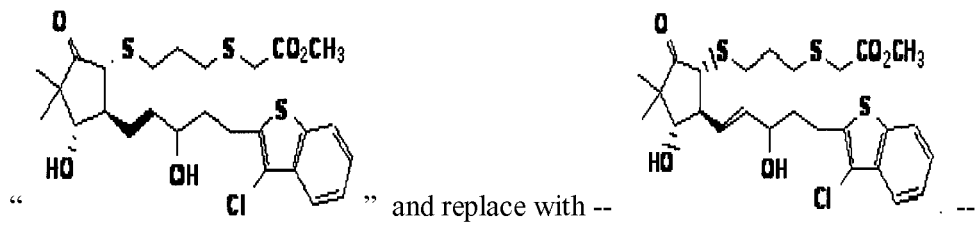

UNITED STATES PATENT AND TRADEMARK OFFICE
CERTIFICATE OF CORRECTION

PATENT NO. : 6,875,787 B2  Page 3 of 8
APPLICATION NO. : 10/365369
DATED : April 5, 2005
INVENTOR(S) : Donde It is certified that error appears in the above-identified patent and that said Letters Patent is hereby corrected as shown below:

In table 1, delete "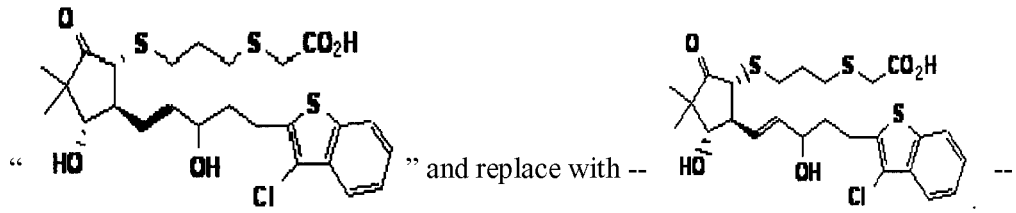" and replace with --  --

In table 1, delete "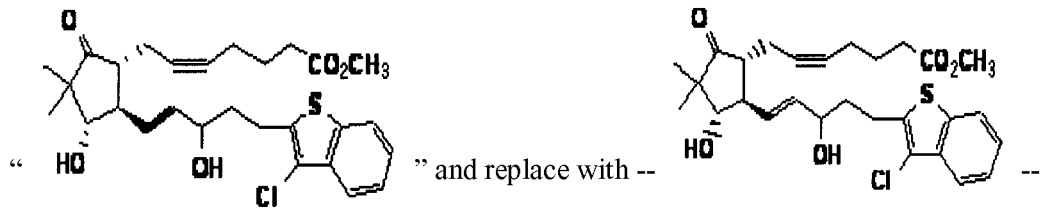" and replace with --  --

In table 1, delete "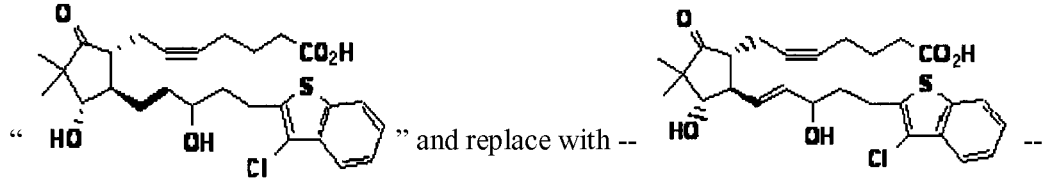" and replace with --  --

In table 1, delete "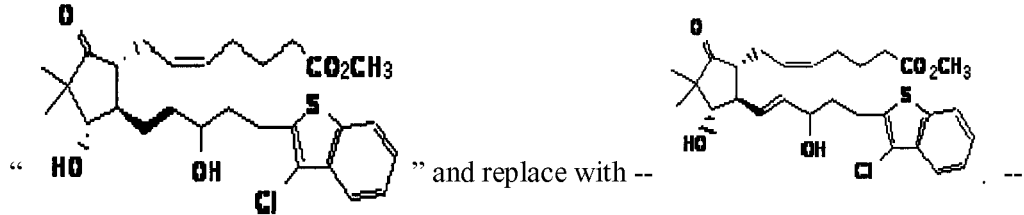" and replace with --  --

UNITED STATES PATENT AND TRADEMARK OFFICE
CERTIFICATE OF CORRECTION

PATENT NO. : 6,875,787 B2 Page 4 of 8
APPLICATION NO. : 10/365369
DATED : April 5, 2005
INVENTOR(S) : Donde It is certified that error appears in the above-identified patent and that said Letters Patent is hereby corrected as shown below:

In table 1, delete

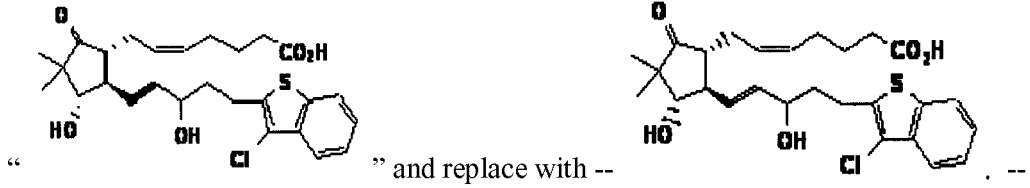

" and replace with --

In table 1, delete

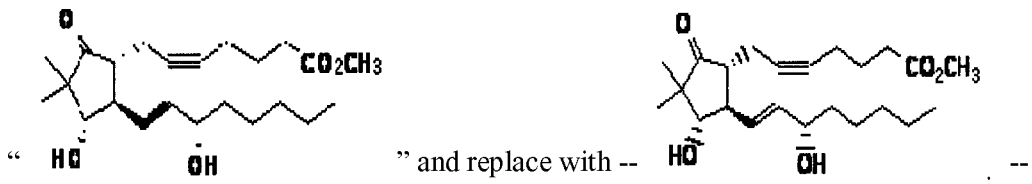

" and replace with --

In table 1, delete

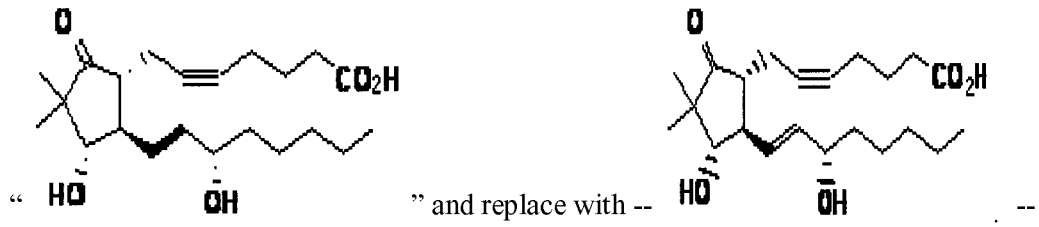

" and replace with --

In table 1, delete

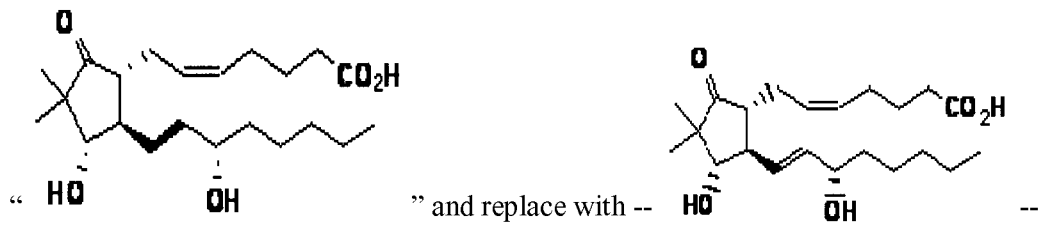

" and replace with --

UNITED STATES PATENT AND TRADEMARK OFFICE
CERTIFICATE OF CORRECTION

PATENT NO. : 6,875,787 B2  Page 5 of 8
APPLICATION NO. : 10/365369
DATED : April 5, 2005
INVENTOR(S) : Donde It is certified that error appears in the above-identified patent and that said Letters Patent is hereby corrected as shown below:

In table 1, delete

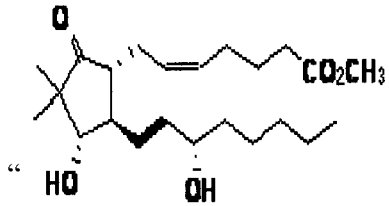 " and replace with -- 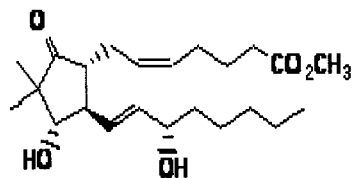 --

In table 1, delete

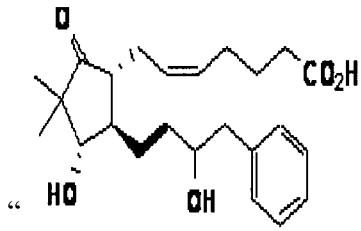 " and replace with -- 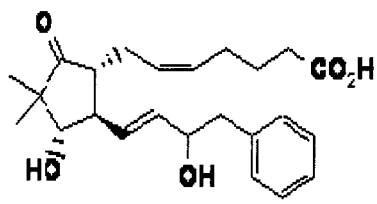 --

In table 1, delete

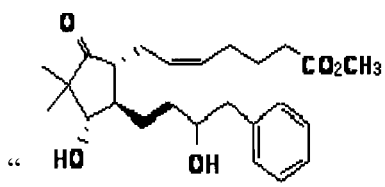 " and replace with -- 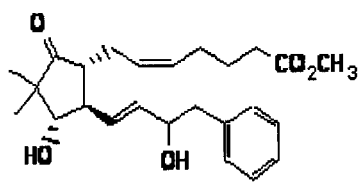 --

In table 1, delete

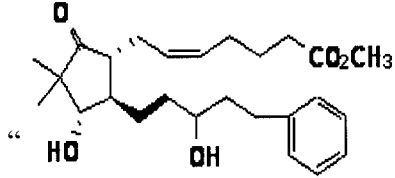 " and replace with -- 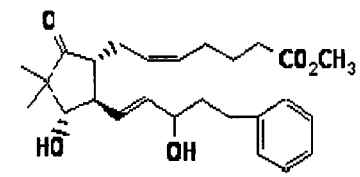 --

UNITED STATES PATENT AND TRADEMARK OFFICE
CERTIFICATE OF CORRECTION

PATENT NO. : 6,875,787 B2
APPLICATION NO. : 10/365369
DATED : April 5, 2005
INVENTOR(S) : Donde It is certified that error appears in the above-identified patent and that said Letters Patent is hereby corrected as shown below:

In table 1, delete

" 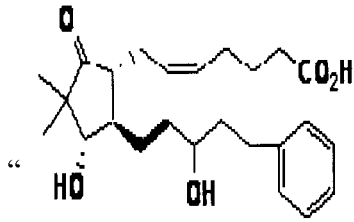 " and replace with -- 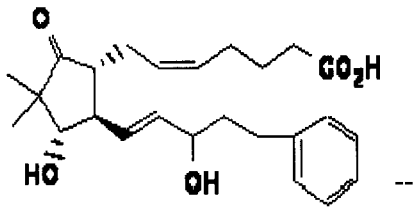 --

In table 1, delete

" 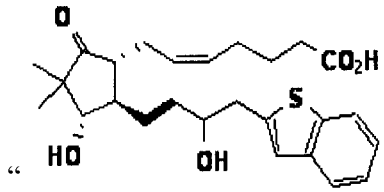 " and repalce with -- 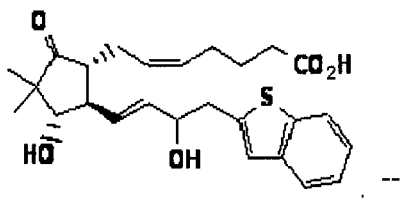 --

In table 1, delete

" 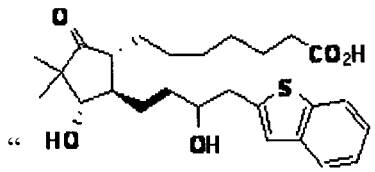 " and replace with -- 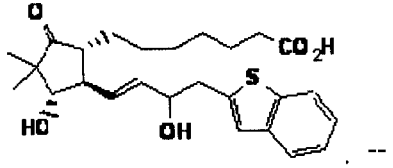 --

In table 1, delete

" 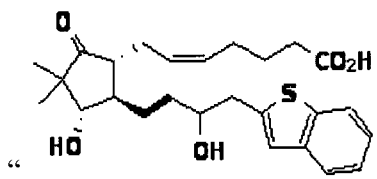 " and replace with -- 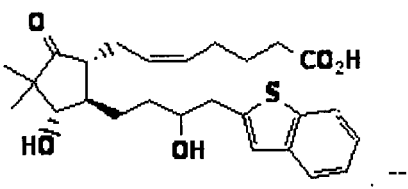 --

UNITED STATES PATENT AND TRADEMARK OFFICE
CERTIFICATE OF CORRECTION

PATENT NO. : 6,875,787 B2
APPLICATION NO. : 10/365369
DATED : April 5, 2005
INVENTOR(S) : Donde It is certified that error appears in the above-identified patent and that said Letters Patent is hereby corrected as shown below:

In table 1, delete

" 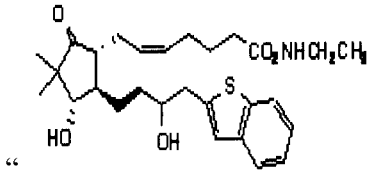 " and replace with -- 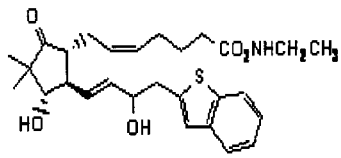 . --

In table 1, delete

" 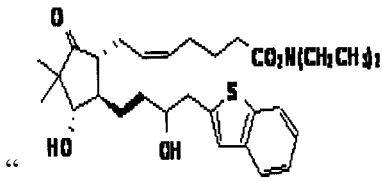 " and replace with -- 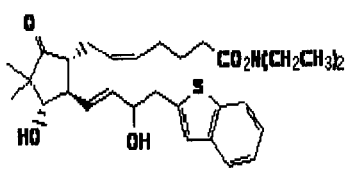 . --

In table 1, delete

" 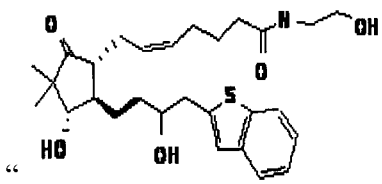 " and replace with -- 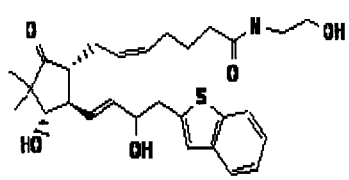 . --

UNITED STATES PATENT AND TRADEMARK OFFICE
CERTIFICATE OF CORRECTION

PATENT NO. : 6,875,787 B2
APPLICATION NO. : 10/365369
DATED : April 5, 2005
INVENTOR(S) : Donde It is certified that error appears in the above-identified patent and that said Letters Patent is hereby corrected as shown below:

In table 1, delete

" 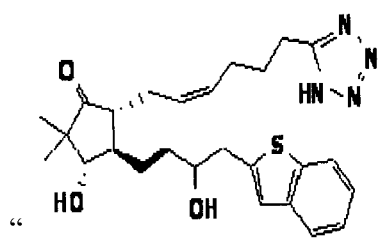 " and replace with -- 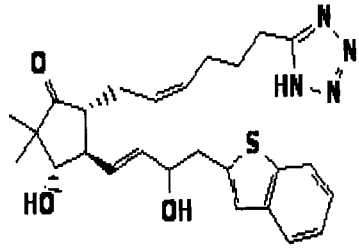 --.

Signed and Sealed this

Twenty-ninth Day of April, 2008

JON W. DUDAS
*Director of the United States Patent and Trademark Office*